(12) United States Patent
Vaara et al.

(10) Patent No.: US 9,090,669 B2
(45) Date of Patent: *Jul. 28, 2015

(54) SHORT FATTY ACID TAIL POLYMYXIN DERIVATIVES AND USES THEREOF

(71) Applicant: Northern Antibiotics Ltd., Helsinki (FI)

(72) Inventors: Martti Sakari Vaara, Helsinki (FI); Timo Ilmari Vaara, Helsinki (FI)

(73) Assignee: NORTHERN ANTIBIOTICS LTD., Helsinki (FI)

(*) Notice: Subject to any disclaimer, the term of this patent is extended or adjusted under 35 U.S.C. 154(b) by 23 days.

This patent is subject to a terminal disclaimer.

(21) Appl. No.: 14/139,231

(22) Filed: Dec. 23, 2013

(65) Prior Publication Data

US 2014/0142030 A1    May 22, 2014

Related U.S. Application Data

(63) Continuation of application No. 13/462,389, filed on May 2, 2012, now Pat. No. 8,642,535, which is a continuation of application No. 12/366,213, filed on Feb. 5, 2009, now Pat. No. 8,193,148.

(60) Provisional application No. 61/127,933, filed on May 16, 2008, provisional application No. 61/065,214, filed on Feb. 8, 2008.

(51) Int. Cl.
  *C07K 7/62*     (2006.01)
  *C12Q 1/18*     (2006.01)
  *A61K 38/00*    (2006.01)

(52) U.S. Cl.
  CPC ... *C07K 7/62* (2013.01); *C12Q 1/18* (2013.01); *A61K 38/00* (2013.01); *G01N 2500/00* (2013.01)

(58) Field of Classification Search
  CPC ....................................................... C07K 7/62
  See application file for complete search history.

(56) References Cited

U.S. PATENT DOCUMENTS

| | | | |
|---|---|---|---|
| 4,485,039 | A | 11/1984 | Hruby |
| 4,510,132 | A | 4/1985 | Vaara |
| 5,620,955 | A | 4/1997 | Knight |
| 7,807,637 | B2 | 10/2010 | Vaara |
| 8,193,148 | B2 | 6/2012 | Vaara |
| 2004/0082505 | A1 | 4/2004 | Ofek et al. |
| 2006/0004185 | A1 | 1/2006 | Leese et al. |
| 2009/0215677 | A1 | 8/2009 | Vaara et al. |
| 2010/0292136 | A1 | 11/2010 | Vaara et al. |

FOREIGN PATENT DOCUMENTS

| | | |
|---|---|---|
| DE | 1906699 B1 | 2/1970 |
| GB | 1323362 B3 | 7/1973 |
| JP | 71-15630 B2 | 4/1971 |
| JP | 72-51356 B4 | 12/1982 |
| WO | 02/055543 A2 | 7/2002 |

OTHER PUBLICATIONS

Ali, Feda' Emad Atta et al. 'Pharmacokinetics of Novel Antimicrobial Cationic Peptides NAB 7061 and NAB 739 in Rats Following Intravenous Administration'. Journal of Antimicrobial Chemotherapy. 2009, vol. 64, pp. 1067-1070.

Chihara, Shiro et al. 'Chemical Synthesis, Isolation and Characterization of a-N-Fattacyl Colistin Nonapeptide with Special Reference to the Correlation Between Antimicrobial Activity and Carbon Number of a Fattyacyl Moiety'. Agricultural and Biological Chemistry. 1974, vol. 38, No. 3, pp. 521-529.

Chihara, Shiro et al. 'Enzymatic Degradation of Colistin Isolation and Identification of a-N-Acyl a,y-Diaminobutyric Acid and Colistin Nonapeptide'. Agricultural and Biological Chemistry. 1973, vol. 37, No. 11, pp. 2455-2463.

Clausell, A et al. 'Influence of Polymyxins on the Structural Dynamics of *Escherichia coli* Lipid Membranes'. Talanta. 2003, vol. 60, pp. 225-234.

Clausell, A et al. 'Gram-negative Outer and Inner Membrane Models: Insertion of the Cyclic Cationic Lipopeptides'. The Journal of Physical Chemistry B. 2007, vol. 111, pp. 551-563.

De Visser, P.C. et al. 'Solid-phase Synthesis of Polymyxin B1 and Analogues Via a Safety-catch Approach'. Journal of Peptide Research. 2003, vol. 61, pp. 298-306.

Kato, Toshiyuki et al. 'The Structure of Octapeptin D (Studies on Antibiotics from the Genus *Bacillus* XXVIII)'. The Journal of Antibiotics. 1980, vol. 33, No. 2, pp. 186-191.

Kimura, Yukio et al. 'Polymyxin B Octapeptide and Polymyxin B Heptapeptide are Potent Outer Membrane Permeability-increasing Agents'. The Journal of Antibiotics. 1992, vol. 45, No. 5, pp. 742-749.

Kurihara, Tozaburo et al. 'Studies on the Compounds Related to Colistin. XI. On the Chemical Deacylation of Colistin and Colistin Derivatives'. Yakugaku Zasshi. 1974, vol. 94, No. 11, pp. 1491-1494.

Li, Jian et al. 'A Simple Method for the Assay of Colistin in Human Plasma, Using Pre-column Derivatization with 9-fluorenylmethyl chloroformate in Solid-phase Extraction Catridges and Reversed-phase High-performance Liquid Chromatography'. Journal of Chromatography B. 2001, vol. 761, pp. 167-175.

(Continued)

*Primary Examiner* — Christina Bradley
(74) *Attorney, Agent, or Firm* — Lathrop & Gage LLP

(57) ABSTRACT

The present invention relates to a polymyxin derivative wherein the derivative has a total of three positive charges at physiological pH and wherein the terminal moiety (D) of the derivative comprises a total of 1 to 5 carbon atoms The invention also relates to a method of treating a subject for a gram-negative bacterial infection by administering a polymyxin derivative of the invention in combination with a second antibacterial agent. Finally, the invention relates to a process for preparing such polymyxin derivatives.

12 Claims, No Drawings

(56) References Cited

OTHER PUBLICATIONS

Li, Jian et al. 'Pharmacokinetics of Colistin Methanesulphonate and Colistin in Rats Following an Intravenous Dose of Colistin Methanesulphonate'. Journal of Antimicrobial Chemotherapy. 2004, vol. 53, pp. 837-840.

Li, Jian et al. 'Use of High-performance Liquid Chromatography to Study the Pharmacokinetics of Colistin Sulfate in Rats Following Intravenous Administration'. Antimicrobial Agents and Chemotherapy. 2003, vol. 47, No. 5, pp. 1766-1770.

Nagai, Junya et al. 'Inhibition of Gentamicin Binding to Rat Renal Brush-border Membrane by Megalin ligands and Basic Peptides'. Journal of Controlled Release. 2006, vol. 112, pp. 43-50.

Nikaido, Hiroshi et al. 'Molecular Basis of Bacterial Outer Membrane Permeability'. Microbiological Reviews. 1985, vol. 49, No. 1, pp. 1-32.

Nikaido, Hiroshi et al. 'Molecular Basis of Bacterial Outer Membrane Permeability Revisited'. Microbiological Reviews. 2003, vol. 67, No. 4, pp. 593-656.

O'Dowd et al. 'Preparation of tetra-Boc-protected Polymyxin B nonapeptide'. Tetrahedron Letters. 2007, vol. 48, pp. 2003-2005.

Okimura, Keiko et al. 'Chemical Conversion of Natural Polymyxin B and Colistin to Their N-Terminal Derivatives'. Bulletin of the Chemical Society of Japan. 2007, vol. 80, No. 3, pp. 543-552.

Potter, Ross et al. 'Inhibition of Food borne Bacteria by Native and Modified Protamine: Importance of Electrostatic Interactions'. International Journal of Food Microbiology. 2005, vol. 103, pp. 23-34.

Rose, Frank et al. 'Targeting Lipopolysaccharides by the Nontoxic Polymyxin B Nonapeptides Sensitizes Resistant *Escherichia coli* to the Bactericidal Effect of Human Neutrophils'. The Journal of Infectious Diseases. 2000, vol. 182, pp. 191-199.

Sakura, Naoki et al. 'The Contribution of the N-Terminal Structure of Polymyxin B Peptides to Antimicrobial and Lipopolysaccharide Binding Activity'. Bulletin of the Chemical Society of Japan. 2004, vol. 77, pp. 1915-1924.

Shoji et al. 'The Structure of Polymyxin S1 Studies on Antibiotics From the Genus *Bacillus*. XXI'. Journal of Antibiotics. 1977, vol. 12, pp. 1035-1041.

Shoji, Jun'Ichi et al. 'Isolation of Octapeptin D (Studies on Antibiotics from the Genus *Bacillus*. XXVII)'. The Journal of Antibiotics. 1980, vol. 33, No. 2, pp. 182-185.

Srinivasa, B.R. et al. 'Chemical Modification of Peptide Antibiotics: Part VI—Biological Activity of Derivatives of Polymyxin B'. Indian Journal of Biochemistry and Biophysics. 1978, vol. 14, pp. 54-58.

Srinivasa, B.R. et al. 'Deacylation of Polymyxin B by Hydrazine & Solvolysis'. Indian Journal of Biochemistry and Biophysics. 1980, vol. 17, pp. 298-302.

Srinivasa, B.R. et al. 'Essential Amino Groups of Polymyxin B'. Indian Journal of Biochemistry and Biophysics. 1980, vol. 17, pp. 112-118.

Srinivasa, B.R. et al. 'The Polymyxins'. Journal of Scientific and Industrial Research. 1979, vol. 38, pp. 695-709.

Storm, Daniel R. et al. 'Polymyxin and Related Peptide Antibiotics'. Annual Review of Biochemistry. 1977, vol. 46, pp. 723-763.

Teuber, Michael et al. 'Preparation of Biologically Active mono-N-acetyl(14C)-derivatives of the Membrane-specific Polypeptide antibiotic Polymyxin B'. Z. Naturforsch. B. 1970, vol. 25, No. 1 pp. 117.

Thomas, Celestine J. et al. 'Kinetics of the Interaction of Endotoxin with Polymyxin B and its Analogues: A Surface Plasmon Resonance Analysis'. FEBS Letters. 1999, vol. 445, pp. 420-424.

Tseubery, Haim et al. 'Modulation of the Hydrophobic Domain of Polymyxin B Nonapeptide: Effect on Outer Membrane Permeabilization and Lipopolysaccharide Neutralization'. Molecular Pharmacology. 2002, vol. 62, No. 5, pp. 1036-1042.

Tseubery, Haim et al. 'Neopeptide Antibiotics That Function as Opsonins and Membraine-permeabilizing Agents for Gram-negative Bacteria'. Antimicrobial Agents and Chemotherapy. 2005, vol. 49, No. 8, pp. 3122-3128.

Tseubery, Haim et al. 'N-terminal Modifications of Polymyxin B nonpeptide and Their Effect on Antibacterial Activitiy'. Peptides. 2001, vol. 22, pp. 1675-1681.

Tseubery, Haim et al. 'Structure-Function Studies of Polymyxin B Nonapeptide: Implications to Sensitization of Gram-negative Bacteria'. Journal of Medicinal Chemistry. 2000, vol. 43, pp. 3085-3092.

Vaara, Martti et al. 'An Outer Membrane-disorganizing Peptide PMBN Sensitizes *E. coli* Strains to Serum Bactericidal Action'. The Journal of Immunology. 1984, vol. 132, No. 5, pp. 2582-2589.

Vaara, Martti et al. 'Antibiotic-Supersusceptible Mutants of *Escherichia coli* and *Salmonella* typhimurium'. Antimicrobial Agents and Chemotherapy. 1993, vol. 37, No. 11, pp. 2255-2260.

Vaara, Martti et al. 'Group of Peptides That Act Synergistically with Hydrophobic Antibiotics Against Gram-negative Enteric Bacteria'. Antimicrobial Agents and Chemotherapy. 1996, vol. 40, No. 8, pp. 1801-1805.

Vaara, Martti et al. 'Polycations as Outer Membrane-disorganizing Agents'. Antimicrobial Agents and Chemotherapy. 1983, vol. 24, No. 1, pp. 114-122.

Vaara, Martti et al. 'Polycations Sensitize Enteric Bacteria to Antibiotics'. Antimicrobial Agents and Chemotherapy. 1983, vol. 24, No. 1, pp. 107-113.

Vaara, Martti et al. 'Sensitization of Gram-negative Bacteria to Antibiotics and Complement by a Nontoxic Oligopeptide'. Nature. 1983, vol. 303, pp. 526-528.

Vaara, Martti. 'Agents That Increase the Permeability of the Bacterial Outer Membrane'. Microbiological Reviews. 1992, vol. 56, No. 3, pp. 395-411.

Vaara, Martii. 'Lipopolysaccharide and the Permeability of the Bacterial Outer Membrane'. Entotoxin in Health and Disease, Chpt. 2, Helmut Brade Ed. pp. 31-38. 1999.

Viljanen, Petri et al. 'The Outer Membrane Permeability-Increasing Action of Deacylpolymyxins'. The Journal of Antibiotics. 1991, vol. 44, No. 5, pp. 517-523.

Weinstein, Jay et al. 'Selective Chemical Modifications of Polymyxin B'. Bioorganic and Medicinal Chemistry Letter. 1998, vol. 8, pp. 3391-3396.

SHORT FATTY ACID TAIL POLYMYXIN DERIVATIVES AND USES THEREOF

RELATED APPLICATION

This application claims priority to U.S. Provisional Application Ser. No. 61/065,214, filed on Feb. 8, 2008, and U.S. Provisional Application Ser. No. 61/127,933, filed on May 16, 2008, the entire contents of which are hereby incorporated herein by reference.

TECHNICAL FIELD

The present invention relates to polymyxin derivatives and to uses thereof in the treatment of infections caused by Gram-negative bacteria. The polymyxin derivatives of the present invention are especially useful in sensitizing bacteria to enhance the effects of other antibacterial agents.

BACKGROUND

Sepsis kills more than 215,000 Americans each year. It is estimated that 750,000 Americans are infected with severe sepsis and 29% of them die from it each year. Sepsis deaths make 9% of all death cases in the U.S. Sepsis kills as many Americans as myocardial infections, even more than traffic accidents.

Two to three million Americans acquire a hospital infection each year and 10% of these infections progress to sepsis. More than 90,000 of these patients die from sepsis infected in hospitals.

Severe sepsis and septic shock (severe sepsis combined with low blood pressure) took up to 135,000 lives each year in the intensive care units (ICU) in the European Union according to the OECD Health Report of 2000. In Britain, 5,000 out of 100,000 patients who acquired a hospital infection die from sepsis every year in acute care hospitals belonging to the NHS organisation.

The death toll has increased year after year due to the fact that the number of patients predisposed to sepsis, such as the elderly, premature neonates, and cancer patients, has increased, not least because many serious illnesses are more treatable than before. Also the use of invasive medical devices and aggressive procedures has increased.

Gram-negative bacteria cause more than 40% of all septicemic infections and many of the Gram-negative bacteria are extremely multiresistant. Gram-negative bacteria provide a harder challenge in therapy than Gram-positives, as they possess a unique structure, the outer membrane, as their outermost structure. Lipopolysaccharide molecules located on the outer membrane inhibit the diffusion of many antibacterial agents deeper into the cell, where their ultimate targets are located. More than 95% of the novel antibacterial agents isolated from nature or chemically synthesized in 1972-1991 lacked activity against Gram-negatives (Vaara 1993).

Polymyxins are a group of closely related antibiotic substances produced by strains of *Paenibacillus polymyxa* and related organisms. These cationic drugs are relatively simple peptides with molecular weights of about 1000. Polymyxins, such as polymyxin B, are decapeptide antibiotics, i.e., they are made of ten (10) aminoacyl residues. They are bactericidal and especially effective against Gram-negative bacteria such as *Escherichia coli* and other species of Enterobacteriaceae, *Pseudomonas, Acinetobacter baumannii*, and others. However, polymyxins have severe adverse effects, including nephrotoxicity and neurotoxicity. These drugs thus have limited use as therapeutic agents because of high systemic toxicity.

Polymyxins have been used in the therapy of serious infections caused by those bacteria, but because of the toxicity, their use was largely abandoned in the 70's when newer, better tolerated antibiotics were developed. The recent emergence of multiresistant strains of Gram-negative bacteria has necessitated the therapeutic use of polymyxins as the last resort, in spite of their toxicity, and as many of the less toxic antibiotics have already lost their effectiveness against particular strains of the said bacteria, the use of polymyxins has again increased.

Accordingly, polymyxins have now been recalled to the therapeutic arsenal, although, due to their toxicity, on a very limited scale. Their systemic (i.e., non-topical) use is, however, largely restricted to the therapy of life-threatening infections caused by multiply resistant strains of *Ps. aeruginosa* and *A. baumannii* as well as by carbapenem-resistant enteric bacteria.

Polymyxins consist of a cyclic heptapeptide part and a linear part consisting of a tripeptide portion and a hydrophobic fatty acid tail linked to the α-amino group of the N-terminal amino acid residue of the tripeptide and may be represented by the general formula:

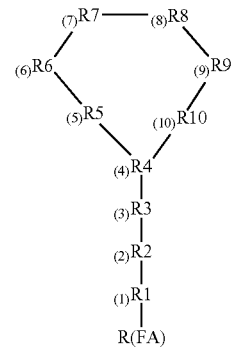

wherein R1-R3 represent the tripeptide side chain portion; R4-R10 the heptapeptide ring portion and R(FA) represents the hydrophobic fatty acid tail linked to the α-amino group of the N-terminal amino acid residue of the tripeptide.

The polymyxin group includes the following polymyxins: A1, A2, B1-B6, IL-polymyxin B1, C, D1, D2, E1, E2, F, K1, K2, M, P1, P2, S, and T (Storm et al. 1977; Srinivasa and Ramachandran 1979). All polymyxins are polycationic and possess five (5) positive charges, with the exception of polymyxin D, F, and S which possess four (4) positive charges. It should be noted that modified polymyxins that lack the fatty acid part R(FA) but carry R1-R10 have one additional positive charge when compared to the natural polymyxins they derived from, due to the free α-amino group in the N-terminus of the derivative. Accordingly, for example, such a derivative of polymyxin B or polymyxin E carries six (6) positive charges in total.

The clinically used polymyxin B and polymyxin E differ from each other only in the residue R6, which is D-phenylalanyl residue in polymyxin B and D-leucyl residue in polymyxin E.

Also circulin A and B are classified as polymyxins (Storm et al. 1977). They differ from other polymyxins only in carrying isoleucyl residue in the position R7 whereas other polymyxins have either threonyl or leucyl residue in the said position. For an overview of the structures of some polymyxins, see Table 1.

side chain, as well as molecules in which an inherent hydrophobic amino acid residue (such as DPhe or Leu) has been replaced with another hydrophobic amino acid residue or in

TABLE 1

The structure of selected polymyxins and octapeptin as well as selected derivatives thereof

| Compound | R(FA) | R1 | R2 | R3 | R4 | R5 | R6 | R7 | R8 | R9 | R10 | SEQ ID NO: |
|---|---|---|---|---|---|---|---|---|---|---|---|---|
| Polymyxin B | MO(H)A- | Dab- | Thr- | Dab- | *Dab- | Dab- | D Phe- | Leu- | Dab | Dab | *Thr | 1 |
| Colistin (polymyxin E) | MO(H)A- | Dab- | Thr- | Dab- | *Dab- | Dab- | D Leu- | Leu- | Dab | Dab | *Thr | 17 |
| Colistin sulphomethate | MO(H)A- | sm-Dab- | Thr- | sm-Dab- | *Dab- | Sm-Dab- | D Leu- | Leu- | sm--Dab- | sm--Dab- | *Thr | 18 |
| Polymyxin A | MO(H)A- | Dab- | Thr- | D Dab- | *Dab- | Dab- | D Leu- | Thr- | Dab | Dab | *Thr | 19 |
| Polymyxin M | MOA | Dab- | Thr- | Dab- | *Dab- | Dab- | D Leu- | Thr- | Dab | Dab | *Thr | 20 |
| Polymyxin D | MO(H)A- | Dab- | Thr- | D-Ser- | *Dab- | Dab- | D Leu- | Thr- | Dab | Dab | *Thr | 21 |
| Circulin A | MOA | Dab- | Thr- | Dab- | *Dab- | Dab- | D Leu- | Ile- | Dab | Dab | *Thr | 22 |
| Octapeptin A | OHMDA | — | — | Dab- | *Dab- | Dab- | D Leu- | Leu- | Dab | Dab | *Leu | 23 |
| Deacylcolistin (DAC) | | Dab- | Thr- | Dab- | *Dab- | Dab- | D Leu- | Leu- | Dab | Dab | *Thr | 24 |
| Polymyxin E nonapeptide (PMEN) | | | Thr- | Dab- | *Dab- | Dab- | D-Leu- | Leu- | Dab | Dab | *Thr | 25 |
| Deacylpolymyxin B (DAPB) | | Dab- | Thr- | Dab- | *Dab- | Dab- | D Phe- | Leu- | Dab | Dab | *Thr | 26 |
| Polymyxin B nonapeptide (PMBN) | | | Thr- | Dab- | *Dab- | Dab- | D Phe- | Leu- | Dab | Dab | *Thr | 4 |
| Polymyxin B octapeptide (PMBO) | | | | Dab- | *Dab- | Dab- | D Phe- | Leu- | Dab | Dab | *Thr | 27 |
| Polymyxin B heptapeptide (PMHP) | | | | | *Dab- | Dab- | D Phe- | Leu- | Dab | Dab | *Thr | 5 |

Polymyxin B is represented by the following formula:

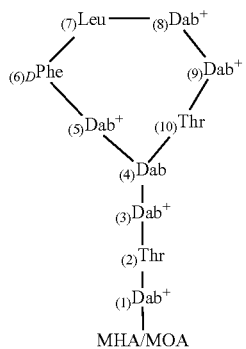

Commercially available polymyxin B is a mixture, where R-FA is predominantly 6-methyloctanoyl (6-MOA, in polymyxin B1) but may also be a related fatty acyl such as 6-methylheptanoyl (6-MHA, in polymyxin B2), α-tanoyl (in polymyxin B3), or heptanoyl (polymyxin B4) (Sakura et al. 2004). All these variants are equally potent against Gram-negatives such as E. coli (Sakura et al. 2004). Quite analogously, in polymyxin E1 (colistin A) and in circulin A the R-FA is 6-MOA and in polymyxin E2 (colistin B) and in circulin B the R-FA is 6-MHA. Numerous researchers have attached various hydrophobic moieties including various fatty acyl residues to the N-terminus of polymyxin derivatives and analogues and have shown that the resulting derivatives have potent antibacterial activity (Chihara et al. 1973, Sakura et al. 2004 and in US patent publication 2006004185. Even the derivative that carries the bulky hydrophobic 9-fluorenylmethoxycarbonyl residue as the R-FA is almost as potent as polymyxin B in inhibiting the growth of E. coli and other Gram-negative bacteria (Tsubery et al. 2001).

For biological activity the heptapeptide ring structure is essential (Storm et al. 1997). A derivative with an octapeptide ring is significantly less active as an antibiotic.

Multiple modifications of polymyxins and multiple polymyxin-like synthetic molecules have been made, and with certain limits they have preserved their biological activity. The modifications comprise but are not limited to those in the which the cationic Dab has been replaced with another cationic amino acyl residue, such as Lys, Arg, or ornithine residue (Storm et al. 1997, Tsubery et al. 2000a, Tsubery et al. 2002, US patent publication 2004082505, Sakura et al. 2004, US patent publication 2006004185).

Other modifications that result in microbiologically at least partially active compounds comprise but are not limited to alkanoyl esters where the OH-groups of the threonyl residues form esters with alkanoyls such as propionyl and butyryl (U.S. Pat. No. 3,450,687).

Octapeptins are otherwise identical to polymyxins but have a covalent bond instead of the residues R1-R2 (Table 1). In this invention, the R positions are numbered according to those in the natural polymyxins and thus the only amino acyl residue in the side chain of octapeptins is defined as R3. Accordingly, octapeptins are octapeptides whereas all natural polymyxins are decapeptides, and they possess only four (4) positive charges. The R-FA residues among various octapeptins (A1, A2, A3, B1, B2, B3, C1) include the following: 3-OH-8-methyldecanoic acid, 3-OH-8-methylnonanoic acid, and β-OH-6-methyloctanoic acid. Derivatives that possess a fatty acyl residue with 6 to 18 carbon atoms have a potent antibacterial activity against E. coli (Storm et al. 1977).

The first target of polymyxins in Gram-negative bacteria is their outer membrane (OM) that is an effective permeability barrier against many noxious agents including large (Mw more than 700 d) antibiotics as well as hydrophobic antibiotics. By binding to the lipopolysaccharide (LPS) molecules exposed on the outer surface of the OM, polymyxins damage the structure and function of the OM and, as a result, permeabilize (i.e., make permeable) the OM to polymyxin itself, as well as to many other noxious agents (Nikaido and Vaara 1985, Vaara 1992, Nikaido 2003). The final and lethal target (the bactericidal target) of polymyxins is believed to be the cytoplasmic membrane (the inner membrane) of bacteria.

Numerous efforts have been made to reduce the toxicity of polymyxins. The treatment of polymyxin E (colistin) with formaldehyde and sodium bisulfite yields colistin sulphomethate, in which the free amino groups of the five diaminobutyric acid residues have partially been substituted by sulphomethyl groups (Table 1). The preparations consist of undefined mixtures of the mono-, di-, tri-, tetra-, and penta-substituted compounds. The sulphomethylated preparations, when freshly dissolved in water, initially lack both the antibacterial activity and toxicity of the parent molecule, but when the compounds start decomposing in the solution, in the blood or in the tissues to yield less substituted derivatives and free colistin, both the antibacterial activity and the toxicity are partially brought back. Furthermore, the degree of initial sulphomethylation apparently varies between the commercially available pharmaceutical preparations. Many other ways to block all the free amino groups have been published. Examples comprise but are not limited to the formation of unstable Schiff bases with amino acids (Storm et al. 1977).

Polymyxin E nonapeptide (PMEN, colistin nonapeptide, Table 1), obtained by treating polymyxin E enzymatically and lacking the R-FA and R1, was shown in 1973 to be less toxic than the parent compound in acute toxicity assay (immediate death presumably due to direct neuromuscular blockade) in mice (Chihara et al. 1973). However, it also lacked the antibacterial activity, as measured as its ability to inhibit bacterial growth (Chirara et al. 1973). The role of the linear part may contribute to the antibacterial activity of the polymyxins.

Vaara and Vaara, on the other hand, showed, that polymyxin B nonapeptide (PMBN, Table 1) retains the ability to permeabilize the OM of Gram-negative bacteria (Vaara and Vaara 1983a,b,c; U.S. Pat. No. 4,510,132; Vaara 1992). Accordingly, even though it lacks the direct antibacterial activity (i.e., the ability to inhibit bacterial growth), it is able to sensitize (i.e., make sensitive or, as also termed, make susceptible) the bacteria to many antibacterial agents such as hydrophobic antibiotics as well as large antibiotics and some other noxious agents.

PMBN also sensitizes bacteria to the bactericidal activity of the human complement system, present in fresh human serum as a first-line defence system against invaders (Vaara and Vaara 1983a, Vaara et al. 1984, Vaara 1992). Furthermore, it sensitizes the bacteria to the joint bactericidal activity of serum complement and human polymorphonuclear white cells (Rose et al. 1999).

PMBN resembles PMEN in being less toxic in the acute toxicity assay in mice than unmodified polymyxins. In further toxicological assays, several criteria proved PBMN to be less toxic than its parent compound, but this polymyxin derivative was still judged to be too nephrotoxic for clinical use (Vaara 1992).

PMBN carries five (5) positive charges. Subsequent studies revealed, quite expectedly, that PMEN, also carrying five (5) positive charges as well as deacylpolymyxin B and deacylpolymyxin E, both carrying six (6) positive charges are potent agents to sensitize bacteria to other antibiotics (Viljanen et al. 1991, Vaara 1992). In addition, it has been shown that a structurally further reduced derivative polymyxin B octapeptide (PMBO) retains a very effective permeabilizing activity while polymyxin B heptapeptide (PMBH) is less active (Kimura et al. 1992). PMBN, PMEN and PMBO have five (5) positive charges while PMBH has only four (4) positive charges. This difference may explain the weaker activity of PMBH.

The group of Ofek, Tsubery and Friedkin recently described polymyxin-like peptides that were linked to chemotactic peptides, such as fMLF, that attract polymorphonuclear leucocytes (US patent publication 2004082505, Tsubery et al. 2005). They described peptides fMLF-PMBN, MLF-PMBN, fMLF-PMEN, fMLF-PMBO and MLF-PMBO, all carrying four (4) positive charges, that sensitize Gram-negative bacteria to antibiotics, even though no comparative studies with increasing concentrations of the compounds were published (Tsubery et al. 2005).

In order to study the structures and functional properties of polymyxins, a few works have disclosed, among other compounds, polymyxin derivatives having less than four (4) positive charges.

Teuber (1970) has described the treatment of polymyxin B with acetic anhydride that yields a preparation containing polymyxin B as well as its mono-, di-, tri-, tetra-, and penta-N-acetylated forms. Teuber also separated each group and nonquantitatively reported using an agar diffusion assay that penta-acetylated and tetra-acetylated forms lacked the ability to halt the growth of *Salmonella typhimurium*, whereas di- and monoacetylated forms did have such ability. Triacetylated form had some ability.

Srinivasa and Ramachandran (1978) isolated partially formylated polymyxin B derivatives and showed that a diformyl derivative as well as a triformyl derivative inhibited the growth of *Pseudomonas aeruginosa*. They did not disclose the compounds' ability to sensitize bacteria to antibiotics. Furthermore, in 1980 they showed that the free amino groups of triformylpolymyxin B in residues R1 and R3, as well as the free amino groups of diformylpolymyxin B in residues R1, R3, and R5 are essential while the free amino groups in R8 and R9 are not essential for the growth inhibition (Srinivasa and Ramachandran, 1980a).

A shortened polymyxin B derivative octanoyl polymyxin B heptapeptide has been disclosed by Sakura et al. (2004). The attachment of the α-tanoyl residue to the N-terminus of the residue R4 of the polymyxin B heptapeptide results in a compound having only three (3) positive charges. Sakura et al. found that octanoyl polymyxin B heptapeptide inhibits the growth of bacteria only at a very high concentration (128 μg/ml), whereas the other derivatives such as octanoyl polymyxin B octapeptide and octanoyl polymyxin B nonapeptide, both having four charges (4) were very potent agents to inhibit bacterial growth.

US patent publication 2006004185 recently disclosed certain polymyxin derivatives and intermediates that can be used to synthesize new peptide antibiotics. The antibacterial compounds described possessed four (4) or five (5) positive charges.

Furthermore, closely related polymyxin B and polymyxin $B_1$ compounds have also been disclosed by Okimura et al. (2007) and de Visser et al. (2003). Okimura et al. have studied the chemical conversion of natural polymyxin B and colistin to their N-terminal derivatives and de Visser et al. have studied solid-phase synthesis of polymyxin $B_1$ and analogues via a safety-catch approach. The antibacterial compounds described in these works possessed four (4) or five (5) positive charges.

There is still an urgent need for polymyxin derivatives, which sensitize bacteria to enhance the effects of other antibacterial agents, for effective treatments for bacterial infections, in particular for the infections caused by multiresistant Gram-negative bacteria.

SUMMARY

The present invention relates to a polymyxin derivative wherein the total number of positive charges at physiological pH is three and wherein the derivative has a fatty acid tail (i.e., R(FA) or D) comprising 1 to 5 carbon atoms. It has been found that certain polymyxin derivatives of the invention having fatty acid tails of 1 to 5 carbon atoms may have improved pharmacokinetic properties as compared to native polymyxins, octapeptins, and polymyxin derivatives with longer fatty acid tails. Examples of these pharmacokinetic properties include, but are not limited to, longer serum half life, increased renal clearance, and/or increased urinary recovery.

The present invention pertains, at least in part, to polymyxin derivatives of formula (I):

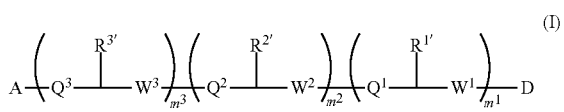

wherein:

A is a polymyxin ring moiety;

D is a terminal moiety comprising 1 to 5 carbon atoms;

$m^1$, $m^2$, and $m^3$ are each independently 0 or 1;

$Q^1$, $Q^2$, and $Q^3$ are each independently $CH_2$, C=O, or C=S;

$W^1$, $W^2$, and $W^3$ are each independently $NR^4$, O, or S;

$R^{1'}$, $R^{2'}$, and $R^{3'}$ are each independently side chains of natural or unnatural amino acids, alkyl, alkenyl, alkyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof, provided that (1) when A is an octapeptin ring, $m^1$ and $m^2$ are 0, $m^3$ is 1, $W^3$ is NH, $Q^3$ is C=O, and $R^{3'}$ is the side chain of diaminobutyric acid (Dab), then D is not $C_2$-$C_5$ acyl, and (2) when D is acetyl, butanoyl or pentanoyl, then $R^{3'}$ is not the side chain of Dab.

The invention is also directed to polymyxin derivatives of formula (II):

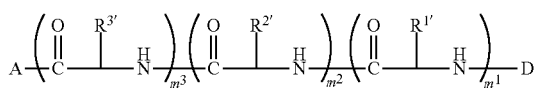

wherein:

A is a polymyxin ring moiety;

D is $R^{12}$—C(=O), $R^{12}$—C(=S), or $R^{12'}$;

$m^1$, $m^2$, and $m^3$ are each independently 0 or 1, provided that at least one of $m^1$, $m^2$, and $m^3$ are 1;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl; and $R^{12}$ is $C_1$-$C_4$ alkyl, $C_2$-$C_4$ alkenyl, or $C_2$-$C_4$ alkynyl, $R^{12'}$ is $C_1$-$C_5$ alkyl, $C_2$-$C_5$ alkenyl, or $C_2$-$C_5$ alkynyl, and pharmaceutically acceptable prodrugs and salts thereof, provided that (1) when A is an octapeptin ring, $m^1$ and $m^2$ are 0, $m^3$ is 1, and $R^{3'}$ is the side chain of diaminobutyric acid (Dab), and D is $R^{12}$—C=O, then $R^{12}$ is not $C_1$-$C_5$ alkyl, and (2) when D is acetyl, butanoyl or pentanoyl, then $R^{3'}$ is not the side chain of Dab.

In another embodiment, the invention also includes polymyxin derivatives of formula (III):

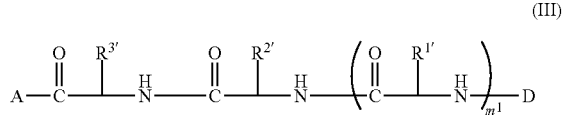

wherein:

A is a polymyxin B or polymyxin E ring moiety;

D is $R^{12}$—C(=O), $R^{12}$—C(=S), or $R^{12'}$;

$m^1$ is 0 or 1;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl, wherein at least one of $R^{2'}$ and $R^{3'}$ comprise a carbamyl, hydroxyl or carboxylate group; and $R^{12}$ is $C_1$-$C_4$ alkyl, $R^{12'}$ is $C_1$-$C_5$ alkyl, and pharmaceutically acceptable prodrugs and salts thereof, provided that when D is acetyl, butanoyl or pentanoyl, then $R^{3'}$ is not the side chain of Dab.

In yet another embodiment, the invention also includes polymyxin derivatives of formula (IV):

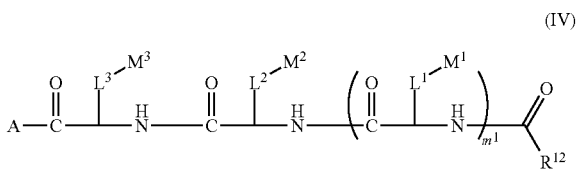

wherein:

A is a polymyxin B or polymyxin E ring moiety;

$m^1$ is 0 or 1;

$L^1$, $L^2$ and $L^3$ are each independently $C_1$-$C_3$ alkyl or a covalent bond;

$M^1$, $M^2$ and $M^3$ are each independently H, C(=O)$NH_2$, C(=O)OH, or —OH;

$R^{12}$ is $C_1$-$C_4$ alkyl, and pharmaceutically acceptable prodrugs and salts thereof, provided that when $R^{12}$ is methyl, propyl or butyl, then $L^3$-$M^3$ is not the side chain of Dab, and wherein said derivative has three positive charges at physiological pH.

In another embodiment, the invention also pertains to polymyxin derivatives of formula (V):

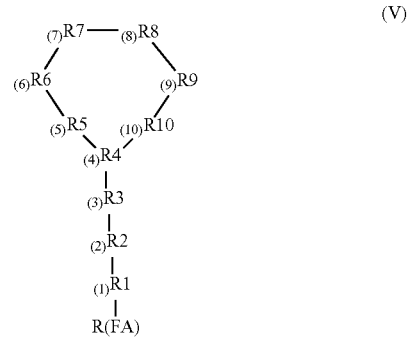

wherein R⁴ is an amino acid residue comprising a functional side chain able to cyclicize the molecule;

R6 and R7 are each independently selected optionally substituted hydrophobic amino acid residues;

R10 is Leu or any non-hydrophobic amino acid residue; and wherein R1 is optional; and wherein R1, R2, R3, R5, R8 and R9 are each independently selected amino acid residues; and wherein R(FA) is an optionally substituted alkanoyl or alkyl residue having a total of 1 to 5 carbon atoms; or a pharmaceutically acceptable salt or prodrug thereof, provided that (1) when R1 and R2 are absent, R3, R4. R5, R8, and R9 are Dab, R6 is D-Leu, R7 is L-Leu or L-Phe, and R10 is Thr, or when R1 and R2 are absent, R3, R4. R5, R8, and R9 are Dab, R6 is D-Phe, R7 is L-Leu, and R10 is Thr, then R(FA) is not an unsubstituted alkanoyl residue, and (2) when R(FA) is acetyl, butanoyl or pentanoyl, then $R^3$ is not Dab.

More specifically, the present invention relates to a derivative, wherein R2-R10 is selected from the group consisting of Thr-DSer-cy[Dab-Dab-DPhe-Leu-Dab-Dab-Thr-] [=SEQ ID NO: 10 or 29] and Thr-DAsn-cy[Dab-Dab-DPhe-Leu-Dab-Dab-Thr-] [=SEQ ID NO: 28].

The invention also relates to a combination product comprising two or more of the derivatives according to the present invention, and to a pharmaceutical composition comprising such derivative(s) or a combination thereof and pharmaceutically acceptable carriers and excipients.

Furthermore, the present invention relates to a method for sensitizing Gram-negative bacteria to an antibacterial agent, comprising administering, simultaneously or sequentially in any order, a therapeutically effective amount of said antibacterial agent and a derivative according to the present invention, wherein said antibacterial agent may be selected from the group consisting of clarithromycin, azithromycin, erythromycin and other macrolides, ketolides, clindamycin and other lincosamines, streptogramins, rifampin, rifabutin, rifalazile and other rifamycins, fusidic acid, mupirocin, oxazolidinones, vancomycin, dalbavancin, telavancin, oritavancin and other glycopeptide antibiotics, fluoroquinolones, bacitracin, tetracycline derivatives, betalactam antibiotics, novobiocin, pleuromutilins, folate synthesis inhibitors, deformylase inhibitors, and bacterial efflux pump inhibitors.

Also provided are methods for developing novel antibiotics; and for sensitizing clinically important Gram-negative bacteria to a host defense mechanism complement present in the serum.

The present invention also provides uses of a polymyxin derivative according to the present invention in the manufacture of medicament for sensitizing Gram-negative bacteria, such e.g., *Escherichia coli, Klebsiella pneumoniae, Klebsiella oxytoca, Enterobacter cloacae, Citrobacter freundii,* and *Acinetobacter baumannii* against antibacterial agents; and for sensitizing Gram-negative bacteria to a host defense mechanism complement present in the serum.

The present invention also pertains to methods of treating Gram-negative infections in a subject comprising administering a derivative of the invention (e.g., a derivative of formulae (I)-(V)) in combination with an antibacterial agent to a subject, such that the subject is treated for the infection.

Finally, the present invention relates to a process for preparing a polymyxin derivative according to the present invention, comprising (A) modifying a natural or synthetic polymyxin or octapeptin compound or a derivative thereof carrying 4 to 5 positively charged residues and a terminal moiety (D) comprising 1 to 5 carbon atoms by replacing 1 to 2 of said positively charged residues by neutral residues or a covalent bond, or by converting 1 to 2 of said positively charged residues into neutral residues in order to obtain a polymyxin derivative of formula (I) carrying 3 positively charged residues and a terminal moiety (D) comprising 1 to 5 carbon atoms, or (B) modifying a natural or synthetic polymyxin or octapeptin compound or a derivative thereof carrying 4 to 5 positively charged residues and a terminal moiety (D) comprising more than 5 carbon atoms by replacing 1 to 2 of said positively charged residues by neutral residues or a covalent bond, or by converting 1 to 2 of said positively charged residues into neutral residues, and by replacing said terminal moiety (D) having more than 5 carbon atoms with a terminal moiety (D) comprising in total 1 to 5 carbon atoms in order to obtain a polymyxin derivative of formula (I) carrying 3 positively charged residues and a terminal moiety (D) comprising in total 1 to 5 carbon atoms, or (C) modifying a natural or synthetic polymyxin or α-tapeptin compound or a derivative thereof carrying 4 to 6 positively charged residues and lacking the terminal moiety (D) by replacing 1 to 3 of said residues by neutral residues, or by a covalent bond, or converting 1 to 3 of said residues into neutral residues, and by introducing a terminal moiety (D) comprising in total 1 to 5 carbon atoms, in order to obtain a polymyxin derivative of formula (I) according to claim 1, carrying 3 positively charged residues and an R(FA) having in total 1 to 5 carbon atoms. In one embodiment of the invention, the terminal moiety D is $R^{12}$—C(=O), $R^{12}$—C(=S), or $R^{12'}$, wherein $R^{12}$ and $R^{12'}$ are defined hereinafter. In another embodiment, the terminal moiety (D) is R(FA), which is an optionally substituted alkanoyl or alkyl residue having a total of 1 to 5 carbon atoms.

DEFINITIONS

"Physiological pH" as used herein refers to a pH value of more than 7.0 and below 7.6, such as a pH value in the range of from 7.1 to 7.5, for example in the range of from 7.2 to 7.4.

"Positive charge" as used herein denote positive charges at the above-defined physiological pH.

"Cationic" molecule as used herein refers to a molecule that contains one or more positive charges.

"Amino acid residue" as used herein refers to any natural, non-natural or modified amino acid residue, either in L- or D-configuration.

"Equivalent residues" as used herein, is intended to include obvious modifications to e.g., amino acids, resulting in non-natural amino acids or derivatives thereof, but retaining the structural and/or functional capacity of the replaced residue.

"Natural polymyxin(s)" as used herein, refers to polymyxins and circulins.

"Polymyxin derivative" refers, for the purpose of this invention, to synthetic or semisynthetic derivatives of natural polymyxins or octapeptins, which have a cyclic heptapeptide (or heptapeptide ring) portion R4-R10 and a side chain linked to the N-terminal aminoacyl residue R4. The side chain may consist of an R(FA)-triaminoacyl(R1-R3), an R(FA)-diaminoacyl(R2-R3), an R(FA)-monoamino-acyl(R3), or of R(FA) alone.

"R(FA)" or "fatty acid tail" as used herein refers to the fatty acid part, i.e., the alkanoyl part of the polymyxin structure, linked to the N-terminal amino acid residue of the linear peptide part (side chain) of the polymyxin or, in the absence of the linear peptide part, to the amino acid residue R4 (the amino acid in 4-position of the cyclic peptide part of the polymyxin). Furthermore, for the purpose of the present invention, R(FA) may also be a related hydrophobic group, such as alkyl. In certain embodiments of the invention, the fatty acid tail may, in certain instances, be a terminal moiety selected from the group consisting of $R^{12}$—(C=O); $R^{12}$—$SO_2$—; $R^{12}$—(C=NH)—; $R^{12}$—NH—(C=S)—; $R^{12}$—NH—(C=O)—; $R^{12}$—NH—(C=NH)—; $R^{12}$—O—(C=S)—; $R^{12}$—O—(C=O); $R^{12}$—P(O)OH—; $R^{12}$—(C=S); and $R^{12'}$, wherein $R^{12}$ and $R^{12'}$ are alkyl, alkenyl, alkynyl, aryl, or aryl alkyl.

"Compounds" as used herein include all stereochemical isomers of said compound.

"Sensitizing activity" or "ability to sensitize" as used herein is intended to include any ability to increase the sensitivity, make sensitive or make susceptible a bacterium to an antibacterial agent.

"Polymyxin ring moiety" or "A" includes the ring portion of polymyxin A, polymyxin B, IL-polymyxin-$B_1$, polymyxin D, polymyxin E, polymyxin F, polymyxin M, polymyxin S, polymyxin T, circulin A, octapeptin A, octapeptin B, octapeptin C, octapeptin D, and derivatives thereof. Examples of derivatives include moieties with modifications which do not substantially effect the ability of the ring moiety to perform its intended function, i.e., as an antibiotic and/or its ability to sensitize bacterium to one or more antibacterial agents. The term "polymyxin B ring moiety" refers to the ring portion of polymyxin B (i.e., cy[DabDab-DPhe-Leu-Dab-Dab-Thr-]). Other examples of polymyxin ring moieties include moieties of the formula:

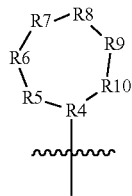

wherein:

$R^4$ is an amino acid residue comprising a functional side chain able to cyclicize the molecule;

$R^5$, $R^8$, and R9 are independently selected amino acid residues;

R6 and R7 are optionally substituted hydrophobic amino acid residues; and

R10 is Leu or any non-hydrophobic amino acid residue. Other examples of R4-R10 are discussed in further detail in Formula (V).

The term "octapeptin ring" refers to the ring portion of native α-tapeptin A (i.e., cy[Dab-Dab-DLeu-LLeu-Dab-Dab-Thr-], i.e., compounds wherein R4, R5, R8, and R9 are Dab, R6 is DLeu, R7 is LLeu, and R10 is Thr), octapeptin B (i.e., cy[Dab-Dab-DLeu-LPhe-Dab-Dab-Thr-], i.e., compounds wherein R4, R5, R8 and R9 are Dab, R6 is DLeu, R7 is LPhe and R10 is Thr), and octapeptin C (i.e., cy[Dab-Dab-DPhe-LLeu-Dab-Dab-Thr-], i.e., compounds wherein R4, R5, R8 and R9 are Dab, R6 is DPhe, R7 is LLeu, and R10 is Thr).

The term "prodrug" includes moieties which are cleaved in vivo to yield an active polymyxin derivative compound of the invention. The prodrugs include moieties which mask or otherwise neutralize the positive charges (i.e., the —$NH_3^+$ or other protonated species) at physiological pH. Once the prodrug is administered to the subject, the prodrug moieties or charge masking moieties will be cleaved or other wise removed to yield the active polymyxin derivative of the invention, optionally with three positive charges at physiological pH.

The term "charge masking moiety" includes moieties that reversibly neutralize positive charges on the derivatives. Preferably, the moieties are cleaved or otherwise disassociated with the positive charges of the polymyxin compound after being administered to a subject. Examples of charge masking moieties include sulfoalkyl (e.g., sulfomethylated derivatives). Other positive charge masking moieties include, but are not limited to, chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis(2-hydroxy-3-naphthoate)).

The term "subject" includes organisms capable of suffering from bacterial infections. Examples of subjects include mammals, e.g., horses, cows, pigs, sheep, goats, cats, dogs, rabbits, ferrets, monkeys, and, preferably, humans.

ABBREVIATIONS

Fatty acids: FA, fatty acyl residue; 6-MOA and MOA, 6-methyloctanoyl residue; 6-MHA and MHA, 6-methylheptanoyl residue; MO(H)A, the mixture of 6-methyloctanoyl, 6-methylheptanoyl and related fatty acyl residues occurring in polymyxin B; OHMDA, 3-OH-8-methyldecanoic acid; OA, octanoyl; DA, decanoyl; Ac, acetyl; Me, methyl.

Amino acids: Dab, α,γ-diamino-n-butyryl residue; fDab, N-γ-formyl diamino-n-butyryl residue; acDab, N-γ-acetyl-diamino-n-butyryl residue; Abu, α-aminobutyryl residue; Asn, aspartyl residue; Thr, threonyl residue; Ser, serinyl residue; Phe, phenylalanyl residue; Leu, leucyl residue; Ile, isoleucyl residue; Ala, alanyl residue; sm-Dab, γ-sulphomethylated α,γ-diamino-n-butyryl residue. One-letter codes for modified amino acyl residues: X, Dab; Z, Abu; B, N-γ-fDab; J, N-γ-acDab.

Peptides: DAPB, deacylpolymyxin B; DAC, deacylcolistin; PMBN, polymyxin B nonapeptide; PMEN, polymyxin E nonapeptide; PMBO, polymyxin B octapeptide; PMHP, polymyxin B heptapeptide.

Other: cy, cyclo (to denote the cyclic part of the peptide, enclosed within brackets); f, formyl; ac, acetyl; sm, sulfomethyl; MS, methanesulfonate; LPS, lipopolysaccharide; OM, outer membrane; MIC, minimum inhibitory concentration; CFU, colony forming unit. The symbol * is used herein to mark the residues between which the heptapeptide ring portion of the compound is closed leaving the remaining part of the molecule as a side chain.

DETAILED DESCRIPTION OF THE INVENTION

It has now been found that certain polymyxin-like compounds containing only three (3) positive charges and having only a short fatty acyl tail R(FA) or terminal moiety (D) (not more than 5 carbon atoms in total) still possess the ability to sensitize Gram-negative bacteria to antibacterial agents such as antibiotics, semisynthetic antibiotics and chemotherapeutic agents as well as to host defence factors such as the complement system of fresh human serum.

Because these novel compounds do not have more than three (3) positive charges, they, in analogy with the polymyxin derivatives described in U.S. patent application Ser. No. 11/891,629, may be less toxic in general and less nephrotoxic in particular than polymyxins and their known derivatives. Similarly, the compounds now invented may reduce less histamine from the host tissues than and have pharmacokinetic properties advantageous over polymyxin B, colistin, and their previously described derivatives. Furthermore, the short R(FA) or terminal moiety (D) may make the novel compounds less toxic in acute toxicity assays, in analogy with polymyxin B nonapeptide and colistin nonapeptide that lack the entire fatty acyl part. Furthermore, the novel compounds may have pharmacokinetic properties that are advantageous over polymyxin derivatives that have a long R(FA) or a terminal moiety (D) with more than five carbon atoms.

In one embodiment, the invention pertains to polymyxin derivatives of the formula (I):

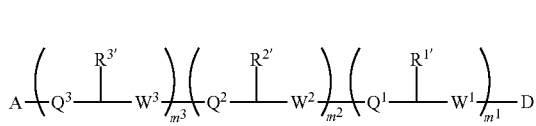

wherein:

A is a polymyxin ring moiety;

D is a terminal moiety comprising 1 to 5 carbon atoms;

$m^1$, $m^2$, and $m^3$ are each independently 0 or 1;

$Q^1$, $Q^2$, and $Q^3$ are each independently $CH_2$, C=O, or C=S;

$W^1$, $W^2$, and $W^3$ are each independently $NR^4$, O, or S;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof, provided that (1) when A is an octapeptin ring, $m^1$ and $m^2$ are 0, $m^3$ is 1, $W^3$ is NH, $Q^3$ is C=O, and $R^{3'}$ is the side chain of diaminobutyric acid (Dab), then D is not $C_2$-$C_5$ acyl, and (2) when D is acetyl, butanoyl or pentanoyl, then $R^{3'}$ is not the side chain of Dab.

In certain embodiments, the compounds of the invention (e.g., derivatives of any one of formulae (I)-(V)) may have at least two but no more than three positive charges at physiological pH. In another embodiment, the compounds have three positive charges at physiological pH.

Examples of prodrugs of these derivatives include those with charge masking moieties which neutralize the three positive charges when administered to the subject which are removed in vivo to yield the compound with three positive charges. Examples of charge masking moieties include sulfoalkyl moieties such as sulfomethyl.

Preferably, the derivatives have three positive charges at physiological pH, as defined above. In certain embodiments of the invention, $IR^{1'}$, $R^{2'}$, and $R^{3'}$ do not comprise positively charged functional groups at physiological pH. $R^{1'}$, $R^{2'}$, and $R^{3'}$ may comprise, for example, one or two or more hydroxyl, carboxylate, carbamyl, thiol, sulfate, sulfonyl, or phosphate groups.

In one embodiment, $m^1$ is 0 and $m^2$ and $m^3$ are each 1. In another, $Q^2$ and $Q^3$ are each C=O and $W^2$ and $W^3$ are each NH.

In certain embodiments, $R^{2'}$ is substituted with one or more groups selected from hydroxyl, carbamyl, carboxylate, thiol, sulfate, sulfonyl, or phosphate groups. Preferably, $R^{2'}$ is substituted with a carbamyl, hydroxyl or carboxylate group. Examples of $R^{2'}$ include substituted alkyl and the side chains of alanine, aminobutyric acid, asparagine, aspartic acid, diaminobutyric acid, glutamic acid, glutamine, serine, or threonine in either the D- or L-configuration. Preferably, $R^{2'}$ is D-alanine, L-serine, or L-threonine.

In certain embodiments, $R^{3'}$ is substituted with one or more groups selected from carbamyl, hydroxyl, carboxylate, thiol, sulfate, sulfonyl, or phosphate. Preferably, $R^{3'}$ is substituted alkyl and may be substituted with a carbamyl, hydroxyl or carboxylate group. $R^{3'}$ may be the side chain of alanine, aminobutyric acid, asparagine, aspartic acid, diaminobutyric acid, glutamic acid, glutamine, serine, or threonine in either the D- or L-configuration. Preferably, $R^{3'}$ is D-asparagine, L- or D-serine.

Examples of A include the ring moiety of polymyxin B (i.e., cy[DabDab-DPhe-Leu-Dab-Dab-Thr-]) and polymyxin E (i.e., cy[Dab-Dab-DLeu-LeuDab-Dab-Thr-].

In a further embodiment, the terminal moiety is selected from the group consisting of $R^{12}$—(C=O); $R^{12}$—$SO_2$—; $R^{12}$—(C=NH)—; $R^{12}$—NH—(C=S)—; $R^{12}$—NH—(C=O)—; $R^{12}$—NH—(C=NH)—; $R^{12}$—O—(C=S)—; $R^{12}$—O—(C=O); $R^{12}$—P(O)OH—; $R^{12}$—(C=S); or $R^{12'}$, wherein $R^{12}$ and $R^{12'}$ are each alkyl, cycloalkyl, alkenyl, alkynyl, aryl, or aryl alkyl. In certain embodiments, D is $R^{12}$—(C=O) or $R^{12}$—(C=S) and $R^{12}$ is methyl, ethyl, propyl, or butyl. Specific examples of D include acetyl, propionyl, butanoyl, and pentanoyl.

In another embodiment, the invention also pertains to polymyxin derivatives of formula (II):

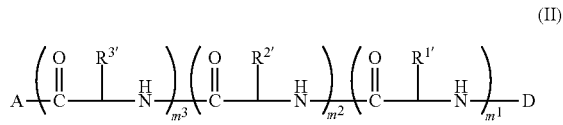

wherein:

A is a polymyxin ring moiety;

D is $R^{12}$—C(=O), $R^{12}$—C(=S) or $R^{12'}$;

$m^1$, $m^2$, and $m^3$ are each independently 0 or 1, provided that at least one of $m^1$, $m^2$, and $m^3$ are 1;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl; and $R^{12}$ is $C_1$-$C_4$ alkyl, $C_2$-$C_4$ alkenyl, or $C_2$-$C_4$ alkynyl, $R^{12'}$ is $C_1$-$C_5$ alkyl, $C_2$-$C_5$ alkenyl, or $C_2$-$C_5$ alkynyl, and pharmaceutically acceptable prodrugs and salts thereof, provided that (1) when A is an octapeptin ring, $m^1$ and $m^2$ are 0, $m^3$ is 1, and $R^{3'}$ is the side chain of diaminobutyric acid (Dab), and D is $R^{12}$—C=O, then $R^{12}$ is not $C_1$-$C_5$ alkyl, and (2) when D is acetyl, butanoyl or pentanoyl, then $R^{3'}$ is not the side chain of Dab.

Preferably, the derivative of formula (II) has three positive charges at physiological pH. In a further embodiment, $m^1$ may be 0 and/or $m^2$ and $m^3$ may each be 1. In a further embodiment, $R^{2'}$ and/or $R^{3'}$ may each independently be substituted alkyl (e.g., substituted with a carbamyl, hydroxyl or carboxylate group). Furthermore, $R^{2'}$ and/or $R^{3'}$ may each be the side chain of serine or threonine (including both D and L configurations). Examples of $R^{2'}$ include the side chains of D-alanine, L-serine and L-threonine. Examples of $R^{3'}$ include the side chains of D-asparagine, L- and D-serine.

In a further embodiment, $R^{12}$ is alkyl and D may be acetyl, propionyl, butanoyl, or pentanoyl.

In another further embodiment, the invention also pertains to polymyxin derivatives of formula (III):

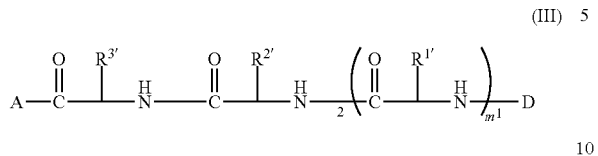

(III)

wherein:

A is a polymyxin B or polymyxin E ring moiety;

D is $R^{12}$—C(=O), $R^{12}$—C(=S) or $R^{12'}$;

$m^1$ is 0 or 1;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl, wherein at least one of $R^{2'}$ and $R^{3'}$ comprise a carbamyl, hydroxyl or carboxylate group; and $R^{12}$ is $C_1$-$C_4$ alkyl, $R^{12'}$ is $C_1$-$C_5$ alkyl, and pharmaceutically acceptable prodrugs and salts thereof, provided that when D is acetyl, butanoyl or pentanoyl, then $R^{3'}$ is not the side chain of Dab.

Preferably, the compounds of the invention have three positive charges at physiological pH, $m^1$ is 0, $R^{2'}$ and $R^{3'}$ are both substituted alkyl, and/or D is acetyl, propionyl, butanoyl, or pentanoyl.

In yet another embodiment, the invention also features a polymyxin derivative of formula (IV):

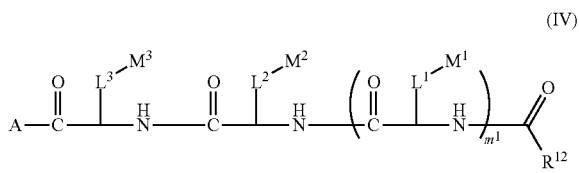

(IV)

wherein:

A is a polymyxin B or polymyxin E ring moiety;

$m^1$ is 0 or 1;

$L^1$, $L^2$ and $L^3$ are each independently $C_1$-$C_3$ alkyl or a covalent bond;

$M^1$, $M^2$ and $M^3$ are each independently H, C(=O)NH$_2$, C(=O)OH, or —OH;

$R^{12}$ is $C_1$-$C_4$ alkyl, and pharmaceutically acceptable prodrugs and salts thereof, provided that when $R^{12}$ is methyl, propyl or butyl, then $L^3$-$M^3$ is not the side chain of Dab.

Preferably, $m^1$ is 0. Examples of $L^2$ include branched alkyl (e.g., —CH(CH$_3$)—). Examples of $M^2$ include OH. Other examples of $L^2$ include —CH$_2$— and other examples of $M^2$ include OH and H. In another embodiment, $L^3$ is —CH$_2$— and $M^3$ is OH. In yet another embodiment, $L^3$ is —CH$_2$—CH$_2$— and $M^3$ is C(=O)NH$_2$. Preferably, the compounds of formula (IV) have three positive charges at physiological pH.

The present invention thus relates to a polymyxin derivative which may be represented by the general formula (V):

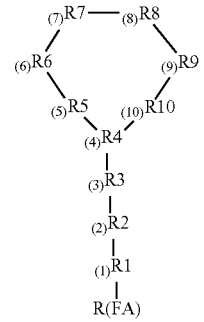

(V)

wherein $R^4$ is an amino acid residue comprising a functional side chain able to cyclicize the molecule;

$R^6$ and $R^7$ are an optionally substituted hydrophobic amino acid residues;

R10 is Leu or any non-hydrophobic amino acid residue; and wherein R1 may be absent; and wherein R1, R2, R3, R5, R8 and R9 are each independently selected amino acids; and wherein R(FA) is an optionally substituted alkanoyl or alkyl residue, having in total 1 to 5 carbon atoms.

or a pharmaceutically acceptable prodrug or salt thereof provided that (1) when R1 and R2 are absent, R3, R4. R5, R8, and R9 are Dab, R6 is D-Leu, R7 is L-Leu or L-Phe, and R10 is Thr or when R1 and R2 are absent, R3, R4. R5, R8, and R9 are Dab, R6 is D-Phe, R7 is L-Leu, and R10 is Thr, then R(FA) is not an unsubstituted alkanoyl residue and (2) when R(FA) is acetyl, butanoyl or pentanoyl, then $R^3$ is not Dab.

In a derivative according to the present invention, R(FA) may be any residue that has small molecular weight and 1 to 5 carbon atoms. The major role of a short R(FA) is to block the free N-terminal amino group of the peptide and thus eliminate one positive charge of the peptide.

Preferably, the compounds of formula (V) may have three positive charges at physiological pH. Furthermore, R1, R2, R3, R5, R8 and R9 may be specifically selected such that the compounds have three positive charges at physiological pH.

The R(FA) is preferably selected from the group consisting of carboxylic acid residues, i.e., alkanoyl groups, or alkyl groups, having in total 1 to 5 carbon atoms. R(FA) is preferably selected from the group consisting of methyl, formyl and acetyl residues. Other useful residues may be selected from propanoyl, butanoyl, isobutanoyl, valeroyl, and isovaleroyl residues. The residues may be branched, straight-chained or cyclic.

R(FA) may also be an unsaturated residue, containing one or more double or triple bonds.

R(FA) may be substituted with substituents readily recognizable by one skilled in the art, provided that R(FA) has no more than 1 to 5 carbon atoms. The substituents may include alkyl, hydroxy and alkoxy. Alkyl is preferably methyl, ethyl, or propyl. Alkoxy is preferably methoxy, ethoxy, or propoxy. A person skilled in the art may readily recognize equivalents of these preferred R(FA) residues and substituents thereof.

In natural polymyxins and octapeptins, R1 is Dab or absent (i.e., replaced by a covalent bond). Examples of known derivatives that have antibacterial activity include those wherein R1 is Ala or a covalent bond.

In a derivative according to the present invention R1, if present, may be any amino acid residue, provided that the total number of positive charges in said derivative does not exceed three and that the total number of positive charges in the side chain portion does not exceed one, and is preferably absent.

In natural polymyxins and octapeptins, R2 is Thr or absent (i.e., replaced by a covalent bond). Examples of known derivatives that have antibacterial activity include those wherein R2 is O-acetyl-Thr, 0-propionyl-Thr, Obutyryl-Thr or a covalent bond.

In a derivative according to the present invention, R2 may be any amino acid residue, preferably hydrophilic or relative hydrophilic, provided that the total number of positive charges in said derivative does not exceed three and that the total number of positive charges in the side chain portion does not exceed one. Examples of R2 include alanine, aminobutyric acid, asparagine, aspartic acid, diaminobutyric acid, glutamic acid, glutamine, serine, or threonine in either D- or L-configuration, A person skilled in the art may also recognize an equivalent residue of Thr to be Ser.

In natural polymyxins and octapeptins, R3 is Dab, DDab or DSer.

In a derivative according to the present invention, R3 may be any amino acid residue, preferably hydrophilic or relatively hydrophilic, provided that the total number of positive charges in said derivative does not exceed three and that the total number of positive charges in the chain portion does not exceed one, and is selected from the group consisting of alanine, aminobutyric acid, asparagine, aspartic acid, diaminobutyric acid, glutamic acid, glutamine, serine, or threonine in either D- or L-configuration.

A person skilled in the art may readily recognize other hydrophilic or relatively hydrophilic residues than these preferred residues R1, R2 and R3, and may select such from a group consisting of e.g. arginine, $N_\omega$-methyl arginine, α-methylaspartate, cysteine, histidine, hydroxylysine, lysine, methionine, ornithine, penicilamine, proline, phosphoserine, phosphothreonine, and tyrosine.

A person skilled in the art may readily note that one of the residues R1, R2 and R3 may not be hydrophilic or relatively hydrophilic, provided that the other two residues are so. Accordingly, R1, R2 and R3 may be selected from a group consisting of e.g. a covalent bond, alanine, 2-aminoadipic acid, α-n-butyric acid, N-(4-aminobutyl)glycine, α-aminobutyric acid, γ-aminobutyric acid, α-amino-caproic acid, aminocyclopropanecarboxylate, aminoisobutyric acid, aminonorbornylcarboxylate, α-amino-n-valeric acid, arginine, $N_\omega$-methyl arginine, asparagine, α-methylaspartate, aspartic acid, N-benzylglycine, N-(2-carbamylethyl)glycine, N-(carbamylethyl)glycine, 1-carboxy-1(2,2-diphenyl ethylamino) cyclopropane, cysteine, $N_\alpha$-methyldiamino-n-butyric acid, $N_\gamma$-acetyldiaminon-butyric acid, $N_\gamma$-formyldiamino-n-butyric acid, $N_\gamma$-methyldiamino-n-butyric acid, N—(N-2,2-diphenylethyl)carbamylmethyl-glycine, N—(N-3,3-diphenylpropyl) carbamylmethyl(1)glycine, N-(3,3-diphenylpropyl)glycine, glutamic acid, glutamine, glycine, t-butylglycine, 2-amino-4-guanidinobutyric acid, N-(3-guanidinopropyl)glycine, histidine, homophenylalanine, isodesmosine, isoleucine, leucine, norleucine, hydroxylysine, $N_\alpha$-methyllysine, lysine, $N_\alpha$-methylhydrooxylysine, $N_\alpha$-methyllysine, $N_\epsilon$-acetylhydroxylysine, $N_\epsilon$-acetyl lysine, $N_\epsilon$-formylhydroxylysine, $N_\epsilon$-formyllysine, $N_\epsilon$-methylhydroxylysine, $N_\epsilon$-methyllysine, methionine, α-methyl-γ-aminobutyrate, α-methyl-aminoisobutyrate, α-methylcyclohexylalanine, α-napthylalanine, norleucine, norvaline, α-methylornithine, $N_\alpha$-methylornithine, $N_\delta$-acetylornithine, $N_\delta$-formyl-ornithine, $N_\delta$-methylornithine, ornithine, penicilamine, phenylalanine, hydroxyproline, proline, $N_\alpha$-methyl-diamino-n-propionic acid, $N_\beta$-acetyldiamino-n-propionic acid, $N_\beta$-formyldiaminon-propionic acid, $N_\beta$-methyldiamino-n-propionic acid, phosphoserine, serine, phosphothreonine, threonine, tryptophan, tyrosine, norvaline, and valine.

In natural polymyxins and octapeptins, R4 is Dab. Examples of synthetic derivatives that have antibacterial activity include those wherein R4 is Lys.

In a derivative according to the present invention R4 is an amino acid residue comprising a functional side chain able to cyclicize the molecule, and may be selected from the group of equivalent residues consisting of Lys, hydroxylysine, ornithine, Glu, Asp, Dab, diaminopropionic acid, Thr, Ser and Cys, preferably Dab.

In natural polymyxins and octapeptins, R5, R8 and R9 are Dab. Examples of synthetic derivatives that have antibacterial activity include those wherein R5, R8, and R9 may be Lys or 2-amino-4-guanidino butyric acid.

In a derivative according to the present invention R5, R8 and R9 may be a positively charged or a neutral amino acid residue, preferably Dab, provided that the total number of positive charges in said derivative does not exceed three.

A person skilled in the art, may readily recognize equivalent residues of these preferred residues, and may select such from a group consisting of e.g. diaminobutyric acid, diaminopropionic acid, lysine, hydroxylysine, or nithine, 2-amino-4-guanidinobutyric acid, glycine, alanine, valine, leucine, isoleucine, phenylalanine, D-phenylalanine, methionine, threonine, serine, α-amino-n-butyric acid, α-amino-n-valeric acid, α-amino-caproic acid, $N_\epsilon$-formyllysine, $N_\epsilon$-acetylysine, $N_\epsilon$-methyllysine, $N_\epsilon$-formylhydroxylysine, $N_\epsilon$-acetyl hydroxylysine, $N_\epsilon$-methylhydroxylysine, L-$N_\alpha$-methylhydroxylysine, $N_\gamma$-formyl diamino-n-butyric acid, $N_\gamma$-acetyldiamino-n-butyric acid, $N_\gamma$-methyldiamino-n-butyric acid, $N_\beta$-formyldiamino-n-propionic acid, D-$N_\beta$-formyldiamino-n-propionic acid, $N_\beta$-acetyldiamino-n-propionic acid, $N_\beta$-methyldiamino-n-propionic acid, $N_\delta$-formylornithine, $N_\delta$-acetylornithine and $N_\delta$-methylornithine.

In natural polymyxins and octapeptins, R6 is DPhe or DLeu and R7 is Leu, Ile, Phe or Thr. Synthetic derivatives that have antibacterial activity include those wherein R6 is DTrp and wherein R7 is Ala.

In a derivative according to the present invention, R6 is an optionally substituted hydrophobic amino acid residue, preferably DPhe or DLeu, and R7 is an optionally substituted hydrophobic residue, preferably Leu, Thr or Ile.

A person skilled in the art may readily recognize equivalent residues of these preferred hydrophobic residues, and may select such from a group consisting of e.g. phenylalanine, α-amino-n-butyric acid, tryptophane, leucine, methionine, valine, norvaline, norleucine, isoleucine and tyrosine. A person skilled in the art may also recognize the equivalent residue of threonine to be serine.

In natural polymyxins and octapeptins, R10 is Thr and Leu. Examples of known derivatives that have antibacterial activity include those wherein R10 is O-acetyl-Thr, O-propionyl-Thr or O-butyryl-Thr.

In a derivative according to the present invention, R10 is Leu or any non-hydrophobic amino acid residue, provided that that the total number of positive charges in said derivative does not exceed three. Preferably R10 is Thr or Leu.

A person skilled in the art may also recognize the equivalent residue of threonine to be serine.

The three (3) positive charges present in the derivatives according to the invention can be located in the heptapeptide ring portion; or two (2) positive charges can be located in heptapeptide ring portion while the remaining one positive charge is located in the side chain.

In one embodiment, derivatives according to the present invention can be selected from the group of derivatives wherein R2-R10 is selected from the group consisting of Thr-DSer-cy [Dab-Dab-DPhe-Leu-Dab-Dab-Thr-], i.e., SEQ ID NO: 10 or 29; and Thr-DAsn-cy [Dab-Dab-DPhe-Leu-Dab-Dab-Thr-], i.e., SEQ ID NO: 28.

In other embodiments, derivatives according to the present invention can be selected from the group consisting of: acetyl-Thr-DSer-cy[Dab-Dab-DPhe-Leu-Dab-Dab-Thr-], i.e., Ac-SEQ ID NO: 10; and acetyl-Thr-DAsn-cy[Dab-Dab-DPhe-Leu-Dab-Dab-Thr-], i.e., Ac-SEQ ID NO: 28.

As shown in the example section herein, the compounds according to the present invention carrying only three (3) positive charges and having an R(FA) containing 1 to 5 carbon atoms only can be very potent agents to sensitize Gram-negative bacteria to antibacterial agents.

For sensitizing activity at least two (2) and more preferably three (3) positive charges are located in the heptapeptide ring part.

The works of Teuber (1970), Srinivasa and Ramachandran (1980a), and Sakura et al. (2004) disclose, among other polymyxin derivatives, derivatives having only two (2) or three (3) positive charges. However, the compounds carry a fatty acid part R(FA) longer than 5 carbon atoms. On the other hand, polymyxin B nonapeptide and colistin nonapeptide, both previously known effective agents to sensitize Gram-negative bacteria to antibiotics, lack the entire R(FA) part but carry five (5) positive charges.

In certain embodiments of the invention, the polymyxin derivatives of formulae I-V may be administered to a subject in prodrug form. The prodrug may comprise one or more charge masking moieties which mask the positive charges of the compound until after it is administered to the subject.

The present invention in one aspect provides new polymyxin derivatives carrying three (3) positive charges only and an R(FA) containing 1 to 5 carbon atoms only and being capable of sensitizing one or more Gram-negative bacterial species to an antibiotic or antibacterial agent.

The susceptibility of bacteria to an antibacterial agent may be determined by two microbiological methods. A rapid but crude procedure uses commercially available filter paper disks that have been impregnated with a specific quantity of the antibacterial agent. These disks are placed on the surface of agar plates that have been inoculated with a suspension of the organism being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration (MIC).

Derivatives according to the present invention may sensitize clinically important Gram-negative bacteria to antibacterial agents, where said Gram-negative bacteria may be those belonging to the genus of *Acinetobacter, Aeromonas, Alcaligenes, Bordetella, Branhamella, Campylobacter, Citrobacter, Enterobacter, Escherichia, Francisella, Fusobacterium, Haemophilus, Helicobacter, Klebsiella, Legionella, Moraxella, Pasteurella, Plesiomonas, Pseudomonas, Salmonella, Serratia, Shigella*, and *Yersinia* species. The bacteria may be, for example, *Escherichia coli, Klebsiella pneumoniae, Klebsiella oxytoca, Enterobacter cloacae, Enterobacter aerogenes*, other species of *Enterobacter, Citrobacter freundii, Acinetobacter baumannii, Pseudomonas aeruginosa* and other *Pseudomonas* species as well as many other species of non-fermentative Gram-negative bacteria. The bacteria also include Helicobacter pylori, as well as other clinically important Gram-negative bacteria.

The bacterial infections to be treated include, for example, bacteremia, septicemia, skin and soft tissue infection, pneumonia, meningitis, infections in the pelveoperitoneal region, foreign body infection, fever in hematological patient, infection associated with an intravenous line or other catheter, canyl and/or device, infection in gastrointestinal tract, in the eye, or in the ear, superficial skin infection, and colonization of gastrointestinal tract, mucous membranes and/or skin by potentially noxious bacteria.

The bacterial infectious diseases include (but are not limited to) severe hospital-acquired infections, infections of the immunocompromised patients, infections of the organ transplant patients, infections at the intensive care units (ICU), severe infections of burn wounds, severe community-acquired infections, infections of cystic fibrosis patients, as well as infections caused by multi-resistant Gram-negative bacteria.

The present invention is also directed to combinations of two or more derivatives according to the present invention for combination treatment. The combinations may include derivatives having a capability to sensitize different species or strains of Gram-negative bacteria to antibacterial agents.

Another aspect of the present invention is directed to pharmaceutical compositions comprising polymyxin derivatives according to the present invention, their prodrug and salt forms, selected combinations thereof, and optionally an antibacterial agent formulated together with one or more pharmaceutically acceptable carriers and excipients. They facilitate processing of the active compounds into preparations which can be used pharmaceutically and include e.g. diluting, filling, buffering, thickening, wetting, dispersing, solubilizing, suspending, emulsifying, binding, stabilizing, disintegrating, encapsulating, coating, embedding, lubricating, colouring, and flavouring agents as well as absorbents, absorption enhancers, humefactants, preservatives and the like, well-known to a person skilled in the art.

Pharmaceutical compositions include compositions wherein the active ingredients are contained in an amount effective to achieve the intended purpose. More specifically, a therapeutically effective amount in connection with the present invention means an amount of compound effective to sensitize Gram-negative bacteria to antibacterial agents. Determination of a therapeutically effective amount is well within the capability of those skilled in the art of medicine.

Compositions may be produced by processes well known in the art, e.g. by means of conventional mixing, dissolving, encapsulating, entrapping, lyophilizing, emulsifying and granulating processes. The proper formulation is dependent upon the route of administration chosen, and the pharmaceutical composition can be formulated for immediate release or slow release (e.g. in order to prolong the therapeutic effect and/or improve tolerability). Furthermore, the formulations may conveniently be presented in unit dosage form by methods known in the art of pharmacy.

Pharmaceutical compositions according to the present invention include (but are not limited to) those intended for intravenous, intramuscular, oral, or topical administration as well as those being administered as a suppositorium or as an inhalable aerosol. The compositions include intravenous, intramuscular, intraperitoneal, subcutaneous, intramedullary, intrathecal, intraventricular, intranasal, or intraocular injections, inhalable aerosols as well as those intended for rectal, oral, intravaginal, transmucosal or transdermal delivery.

For parenteral administration (e.g. by bolus injection, fast running infusions, or slow infusions), the compounds according to this invention as well as the combinations described above may be formulated as their suitable salt or ester forms in sterile aqueous solutions, preferably physiologically compatible fluids such as saline, 5% dextrose, Ringer's solution, and Hank's solution. The formulation may also include organic solvents such as propylene glycol, polyethylene glycol, propylene glycol or related compounds as well as preservatives and surfactants.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

In addition, the pharmaceutical compositions for parental administration may be suspensions or emulsions in oily or aqueous vehicles, and may contain formulatory agents such as suspending, stabilizing and/or dispersing agents. Suitable lipophilic vehicles and solvents include fatty oils such as natural and/or synthetic fatty acids esters, such as ethyl oleate and triglycerides, or liposomes. The suspensions may contain substances, which increase the viscosity of the suspension, such as sodium carboxymethyl cellulose, sorbitol or dextran.

The parenteral compositions can be presented in unit-dose or multidose sealed containers, such as ampules and vials, and can be stored in a freeze-dried (lyophilized) condition requiring only the addition of the sterile liquid excipient, for example, water, for injections, immediately prior to use.

For oral administration, solid form preparations include e.g. powders, tablets, pills, dragees, lozenges, capsules, cachets, and microgranular preparations. Pharmaceutical preparations can be made using a solid excipient, optionally grinding the resulting mixture, and processing the mixture of granules, after adding suitable auxiliaries if desired, to obtain tablets or dragee cores. A solid carrier/excipient can be one or more substances which may also act as diluents, solubilizers, lubricants, suspending agents, binders, preservatives, flavouring agents, wetting agents, tablet disintegrating agents, or an encapsulating material. Suitable carriers include, but are not limited to, magnesium carbonate, magnesium stearate, talc, dextrose, lactose, pectin, starch, gelatin, tragacanth, methylcellulose, sodium carboxymethylcellulose, a low melting wax, cocoa butter, and the like.

Liquid preparations suitable for oral administration include, e.g., aqueous solutions, syrups, elixirs, aqueous suspensions, emulsions and gels. Aqueous solutions can be prepared by dissolving the active component in water and adding suitable stabilizing and thickening agents as well as colorants and flavours. Aqueous suspensions can be prepared by dispersing the finely divided active component in water with viscous material, such as natural or synthetic gums, resins, methylcellulose, sodium carboxymethylcellulose, and other well known suspending agents. Emulsions may be prepared in solutions in aqueous propylene glycol solutions or may contain emulsifying agents such as lecithin, sorbitan monooleate or acacia.

The compounds according to the invention or combinations described above may also be formulated for topical administration. The active compounds are admixed under sterile conditions with pharmaceutically acceptable carriers/excipients, including any needed buffering agents and preservatives. Ointments, creams and lotions may, for example, be formulated with an aqueous or oily base with the addition of suitable emulsifying, dispersing, suspending, thickening, stabilizing, or coloring agents. Commonly used excipients include animal and vegetable fats and oils, waxes, paraffins, starch, cellulose derivatives, tragacanth, and polyethylene glycol.

Other topical formulations include, but are not limited to, ear-drops, eye-drops and transdermal patches.

For transdermal as well as transmucosal administration, penetrants generally known in the art may be used in the formulation.

For administration by inhalation, the compounds according to this invention and the combinations described above are delivered in the form of an aerosol spray presentation from a ventilator, pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The compounds according to this invention and the combinations described above may also be formulated in rectal compositions such as retention enemas or suppositories, using conventional suppository bases such as cocoa butter, other glycerides, polyethylene glycol, or a suppository wax.

The present invention also relates to a method for using the present polymyxin derivatives or a combination of such derivatives as a part of the clinical treatment of (or a preventive prophylactic regimen for) human or animal subjects suffering of an infectious disease (i.e., a Gram-negative bacterial infection), and comprises administering to said subject an therapeutically effective dose of at least one derivative according to the present invention, in combination with an antibacterial agent.

The present invention also relates to a method of sensitizing Gram-negative bacteria to an antibacterial agent, wherein the derivative according to the present invention is administered simultaneously, or sequentially in any order, with a therapeutically effective amount of said antibacterial agent.

The derivative of the present invention and the antibacterial agent may be administered together as one formulation or by different routes. For example, the polymyxin derivative may be administered intravenously while the antibacterial agent is administered intramuscularly, intravenously, subcutaneously, orally or intraperitoneally. Alternatively, the derivative may be administered intramuscularly or intraperitoneally while the antibacterial agent is administered intravenously, intramuscularly or intraperitoneally, or the derivative may be administered in an aerosolized or nebulized form while the antibacterial agent is administered, e.g., intravenously. The derivative and the antibacterial agents may be administered simultaneously or sequentially, as long as they are given in a manner sufficient to allow both to achieve effective concentrations at the site of infection.

"Therapeutic effectiveness" is based on a successful clinical outcome, and does not require that a derivative according to the present invention, in combination with an antibacterial agent, kills 100% of the bacteria involved in an infection. Successful treatment depends on achieving a level of antibacterial activity at the site of infection, sufficient to inhibit the bacteria in a manner that tips the balance in favor of the host. When host defenses are maximally effective, the antibacterial effect required may be modest. Reducing organism load by even one log (a factor of 10) may permit the host's own defenses to control the infection. In addition, augmenting an early bactericidal/bacteriostatic effect can be more important than long-term bactericidal/bacteriostatic effect. These early events are a significant and critical part of therapeutic success, because they allow time for host defense mechanisms to activate. Increasing the bactericidal rate may be particularly important for infections such as meningitis, bone or joint infections.

The therapeutic effectiveness of an antibacterial agent depends on the susceptibility of the bacterial species to said antibacterial agent at the clinically relevant concentration of the derivative according to this invention. The effect of compounds according to the present invention to improve the therapeutic effectiveness of antibacterial agents in vivo may be demonstrated in vivo animal models, such as mouse peritonitis or rabbit bacteremia assays, and may be predicted on the basis of a variety of in vitro tests, including (1) determinations of the minimum inhibitory concentration (MIC) of an antibacterial agent required to inhibit growth of a Gram-negative bacterium for 24 hours, (2) determinations of the effect of an antibacterial agent on the kinetic growth curve of a Gram-negative bacterium, and (3) checkerboard assays of the MIC of serial dilutions of antibacterial agent alone or in combination with serial dilutions of compound(s). Exemplary models or tests are well known in the art.

Using in vitro determinations of MIC at 24 hours, a derivative according to the present invention may be shown to reduce the MIC of the antibacterial agent. With this result, it is expected that concurrent administration of the compound in vivo will increase susceptibility of a Gram-negative bacterium to the antibacterial agent. A compound according to the present invention may also be shown to reduce the MIC of an antibacterial agent from the range in which the organism is considered clinically resistant to a range in which the organism is considered clinically susceptible. With this result, it is expected that concurrent administration in vivo of the one or more compound(s) according to the present invention with the antibacterial agent will reverse resistance and effectively convert the antibiotic-resistant organism into an antibiotic-susceptible organism.

By measuring the effect of antibacterial agents on the in vitro growth curves of Gram-negative bacteria, in the presence or absence of a compound according to the present invention, the compound may be shown to enhance the early antibacterial effect of antibacterial agents within a period of preferably less than 24 hours. Enhancement of early bactericidal/growth inhibitory effects is important in determining therapeutic outcome.

In a checkerboard assay, the combination of a compound according to the present invention with antibacterial agents may result in a "synergistic" fractional inhibitory concentration index (FICI). The checkerboard method is based on additivity, which assumes that the result observed with multiple drugs is the sum of the separate effects of the drugs being tested; according to this system a FICI of less than 0.5 is scored as synergy, 1 is scored as additive, and greater than 1 but less than 2 is scored as indifferent.

Antibacterial agents suitable for use in combination with derivatives according to the present invention, include e.g. macrolides, such as clarithromycin, azithromycin, and erythromycin, ketolides, lincosamines, such as clindamycin, streptogramins, rifamycins, such as rifampin, rifabutin and rifalazile, fusidic acid, mupirocin, oxazolidinones, glycopeptide antibiotics, such as vancomycin, dalbavancin, telavancin and oritavancin, fluoroquinolones, tetracycline derivatives, hydrophobic derivatives of penicillins, cephalosporins, monobactams, carbapenems, penems and other betalactam antibiotics, novobiocin, pleuromutilins, folate synthesis inhibitors, deformylase inhibitors, and bacterial efflux pump inhibitors. A person skilled in the art of treating Gram-negative infections may easily recognize additional, clinically relevant antibacterial agents that may be useful. Preferably said antibacterial agents are selected from a group of hydrophobic or moderately hydrophobic antibacterial agents against which the outer membrane of Gram-negative bacteria acts as an effective permeability barrier.

The invention also includes the use of the present compounds or combinations thereof to sensitize clinically important bacteria listed herein to the host defence mechanism complement (present in the fresh human and animal serum) by subjecting said bacteria to the action of such compounds during a clinical infection or a suspected infection. The host defence can be exerted, e.g., by the combined action of complement and polymorphonuclear leucocytes.

Those skilled in the art of medicine can readily optimize effective dosages and administration regimens for the compounds according to the present invention as well as for the antibiotics in concurrent administration, taking into account factors well known in the art including type of subject being dosed, age, weight, sex and medical condition of the subject, the route of administration, the renal and hepatic function of the subject, the desired effect, the particular compound according to the present invention employed and the tolerance of the subject to it. Dosages of all antimicrobial agents should be adjusted in patients with renal impairment or hepatic insufficiency, due to the reduced metabolism and/or excretion of the drugs in patients with these conditions. Doses in children should also be reduced, generally according to body weight.

The total daily dose of a derivative according to the present invention administered to a human or an animal can vary, for example, in amounts from 0.1 to 100 mg per kg body weight, preferably from 0.25 to 25 mg per kg body weight.

It will also be recognised by one skilled in the art that the optimal course of treatment, i.e., the number of doses given per day for a defined number of days, will be determined by the nature and extent of the condition being treated, the form, route and site of administration, and the particular patient being treated, and that such optimums can be determined by conventional techniques.

There is also provided a method for assaying a compound according to the present invention, said compound being a derivative of a natural polymyxin or octapeptin, wherein said derivative has a only 3 positive charges and a terminal moiety (D) comprising 1 to 5 carbon atoms, in contrast to the naturally occurring compound from which it is derived, for the ability to sensitize a harmful Gram-negative to antibacterial agents and/or the complement present in the serum, said method comprising the step of contacting the bacterium with said derivative of a natural polymyxin or octapeptin, and identifying derivatives possessing sensitizing activity towards said bacterium.

In a further aspect there is provided a method for developing novel antibiotics comprising the steps of (a) providing a natural polymyxin or octapeptin compound, or a derivative thereof, carrying a total of 4 to 6 positive charges and a terminal moiety (D) comprising 1 to 5 carbon atoms, (b) replacing from 1 to 3 residues carrying one or more positive charges with a residue not having a positive charge, or with a covalent bond, thereby generating a polymyxin derivative carrying 3 positive charges and a terminal moiety (D) comprising 1 to 5 carbon atoms, (c) assaying said polymyxin derivative for the ability to sensitize Gram-negative bacteria to antibacterial agent; and (d) selecting compounds having the ability to sensitize Gram-negative bacteria to an antibacterial agent.

In one embodiment of the method of the invention, the terminal moiety (D) is $R^{12}$—C(=O), $R^{12}$—(C=S), or $R^{12'}$, wherein $R^{12}$ and $R^{12'}$ are as defined above. In another embodiment of the invention, the terminal moiety (D) is R(FA), which is an optionally substituted alkanoyl or alkyl residue having a total of 1 to 5 carbon atoms.

In a still further aspect of the invention there is provided a method for developing novel antibiotics comprising the steps of (a) providing a natural polymyxin or octapeptin compound, or a derivative thereof, carrying a total of 4 or 5 positive charges, or a total of 6 positive charges, as in deacylpolymyxins, and a terminal moiety (D) comprising more than 5 carbon atoms, (b) replacing from 1 to 3 residues carrying one or more positive charges with a residue not having a positive charge, or with a covalent bond, thereby generating a derivative of a polymyxin compound having 3 positive charges, (c) replacing a terminal moiety (D) comprising more than 5 carbon atoms with a terminal moiety (D) comprising 1 to 5 carbon atoms, thereby generating a derivative of a polymyxin compound carrying 3 positive charges and an a terminal moiety (D) comprising 1 to 5 carbon atoms, (d) assaying said polymyxin derivative for the ability to sensitize Gram-negative bacteria to antibacterial agent; and (e) selecting compounds having the ability to sensitize Gram-negative bacteria to an antibacterial agent.

In one embodiment of the method of the invention, the terminal moiety (D) is $R^{12}$—C(=O), $R^{12}$—(C=S), or $R^{12'}$, wherein $R^{12}$ and $R^{12'}$ are as defined above. In another embodiment of the invention, the terminal moiety (D) is R(FA), which is an optionally substituted alkanoyl or alkyl residue having a total of 1 to 5 carbon atoms.

In a still further aspect of the invention there is provided a method for developing novel antibiotics comprising the steps of a) providing a polymyxin or octapeptin compound, or a derivative thereof, having a total of 4 to 6 positive charges and lacking the terminal moiety (D), b) replacing from 1 to 3 residues carrying one or more positive charges with a residue not having a positive charge, or with a covalent bond, thereby generating a derivative of a polymyxin compound carrying 3 positive charges;

c) introducing a terminal moiety (D) comprising 1 to 5 carbon atoms, thereby generating a polymyxin compound carrying 3 positive charges and a terminal moiety (D) comprising of 1 to 5 carbon atoms;

e) assaying said polymyxin derivative for the ability to sensitize Gram-negative bacteria to antibacterial agent; and f) selecting compounds having the ability to sensitize Gram-negative bacteria to an antibacterial agent.

In one embodiment of the method of the invention, the terminal moiety (D) is $R^{12}$—C(=O), $R^{12}$—(C=S), or $R^{12'}$, wherein $R^{12}$ and $R^{12'}$ are as defined above. In another embodiment of the invention, the terminal moiety (D) is R(FA), which is an optionally substituted alkanoyl or alkyl residue having a total of 1 to 5 carbon atoms.

There is also provided in accordance with the present invention a semisynthetic polymyxin derivative obtainable by treating chemically or enzymatically naturally-occurring polymyxins or octapeptins, respectively, or those variants thereof which are manufactured by genetically modified organisms. Chemical treatments include, but are not limited to, those with acetanhydride, formic acid, hydrazine, and oxalic acid. Enzymatic treatments include, but are not limited to, with enzymes such as polymyxin deacylase, ficin, papain, bromelain, subtilopeptidases, subtilisin, colistin hydrolase, and Nagarse.

Preferred compounds according to one embodiment are less cationic than natural polymyxins or octapeptins, carry three (3) positive charges only and an R(FA) having 1 to 5 carbon atoms, and are:

(a) able to sensitize Gram-negative bacteria such as *Escherichia coli, Klebsiella pneumoniae, Klebsiella oxytoca, Enterobacter cloacae, Citrobacter freundii*, and *Acinetobacter baumannii* to antibiotics, and/or (b) less toxic than clinically used polymyxins, as evidenced in in vivo animal model, and/or (c) less nephrotoxic than clinically used polymyxins, as evidenced in an animal model and/or in an in vitro test that measures affinity of the compounds to kidney structures, and/or (d) able to cause less histamine liberation from the tissues than clinically used polymyxins when administered topically or when inhaled as an aerosol, and/or (e) pharmacokinetically more favorable, such as having a longer serum half life, increased renal clearance, increased urinary recovery and/or by being less inactivated by polyanionic tissue and pus constituents than clinically used polymyxins.

In a further embodiment, the compounds of the invention have one or more pharmacokinetically favorable properties as compared to native polymyxins or octapeptins (e.g., polymyxin A, polymyxin B, IL-polymyxin-$B_1$, polymyxin D, polymyxin E, polymyxin F, polymyxin M, polymyxin S, polymyxin T, circulin A, octapeptin A, octapeptin B, octapeptin C, or octapeptin D). Examples of such pharmacokinetically favorable properties include a longer serum half life, increased renal clearance, or increased urinary recovery as compared to native polymyxins or octapeptins (such as polymyxin E).

In a further embodiment, the compounds of the invention may have a greater percent urinary recovery of an administered dose over 24 hours than polymyxin E (colistin). In another further embodiment, the urinary recovery, based on experiments with rats, is about 1% or greater, about 5% or greater, about 10% or greater, about 15% or greater, about 20% or greater, about 25% or greater, about 30% or greater, about 35% or greater, about 40% or greater, about 45% or greater, or about 50% or greater. In contrast, the urinary recovery of polymyxin E (colistin) was determined to be about 0.18±0.14% of dose in 24 hours (Li et al., 2003), using the same dose and procedure.

In another further embodiment, the compounds of the invention may have a greater renal clearance than polymyxin E (colistin) when administered using the same route and dosing. In a further embodiment, the compounds of the invention have a renal clearance, based on experiments with rats, greater than about 0.1 ml/min/kg, greater than about 0.5 ml/min/kg, greater than about 1.0 ml/min/kg, greater than about 2.0 ml/min/kg, greater than about 2.5 ml/min/kg, greater than about 3.0 ml/min/kg, or greater than about 3.5 ml/min/kg. In another further embodiment, the renal clearance of the compounds of the invention may be at least 10 times, at least 50 times, at least 100 times, at least 150 times, at least 200 times, at least 250 times, or at least 300 times that of polymyxin E, when administered at the same dose and administration route.

In another further embodiment, the compounds of the invention may also have one or more pharmacokinetically favorable properties as compared to similar compounds with longer fatty acid tails (i.e., a terminal moiety or R(FA) having more than five carbon atoms). As shown in Example 8, NAB741 has increased renal clearance and increased urinary recovery as compared to NAB739. The compounds are chemically identical except that NAB741 has an acetyl terminal moiety and NAB739 has an octanoyl terminal moiety.

Methods for synthesising compounds according to the present invention include but are not limited to the following described below. For a specific compound to be synthetised, an expert in the art is able to choose the appropriate method.

1. Semisynthetic derivatives of polymyxins and octapeptins that carry an unchanged heptapeptide part and a modified acyl-aminoacyl side chain can be made by the procedures described as follows:

Protection of the free amino groups in the starting material (polymyxin or octapeptin, or modifications thereof) by methods known to those skilled in the art. The protection can be achieved by the use of residues such as t-butoxycarbonyl (tBoc), fluorenylmethoxycarbonyl (Fmoc), benzyloxycarbonyl (CBZ, Z), allyloxycarbonyl (ALOC), 3-pyridyl-N-oxide-methoxycarbonyl (as described in patent publication GB 1323962), by using Schiff bases such as benzaldehyde by the method described in Japanese Patent publication 7115630/1971 or the like which can be removed by conventional conditions compatible with the nature of the product.

In conditions where the poor water solubility occasionally poses a problem in the sub-sequent steps, the protection can be made by using negatively-charged blocking groups such as a sulfonic acid derivative of Fmoc or a carboxylic acid derivative of Fmoc, the method being described in US patent publication 2006004185. The water solubility can also be enhanced by linking a suitable, removable, negatively charged, very hydrophilic blocking group to the OH-group of threonine.

Thereafter, the compound is subjected to an enzymatic treatment with enzymes such as polymyxin deacylase, polymyxin hydrolase, papain, ficin, bromelain, subtilopeptidase, Nagarse or other enzymes that remove a terminal part of the side chain or even the entire side chain of polymyxin or octapeptin compounds. This treatment can optionally be followed by the Edman degradation procedure. The resultant compound lacks the entire side chain and consists of the cyclic heptapeptide part only, but has a free N-terminal alpha amino group.

Alternatively, polymyxins and octapeptins that have amino groups protected by acid-stable groups such as benzyloxycarbonyl can be treated by oxalic acid or formic acid to yield protected deacyl-derivatives, the method being described by Kurihara et al. (1974). The procedure is followed by further enzyme treatment as above and/or by Edman degradation to yield a heptapeptide.

Thereafter, a suitable residue is linked to the free alpha-amino position of the heptapeptide ring portion. The residue might contain an acyl or related residue (R(FA) having in total 1 to 5 carbon atoms), such as methyl, acetyl, propionyl, butanoyl, isobutanoyl, valeroyl, and isovaleroyl residue) as well as amino acid residues, up to three and preferably two residues. For instance, one semisynthetic compound with an acyl group and two amino acid residues can be prepared by adding to the above-described heptapeptide a synthetic N(acyl)-threonyl-D-threonyl residue. This can be achieved by conventional general techniques known to those familiar with the art of organic chemistry, these techniques including the use of N-hydroxysuccinimide-linked residues as described in US 2006004185. In this particular synthesis the procedure may involve the use of N-acetylthreonyl-D-serinyl-N-hydroxysuccinimide.

2. Acylated polymyxin nonapeptides carrying three (3) free amino groups. Polymyxin D possesses only four (4) positive charges and has DSer in the position R3. The free amino groups of polymyxin D can be protected by the means described above. This is followed by an enzymatic treatment and an optional Edman degradation step, to yield a nonapeptide, which can then be acylated by acylisotiocyanate (by the method well-known to a person skilled in the art and described in US 2006004185, by acyl chloride (by the method well-known to a person skilled in the art and described in Chihara et al. 1974), or by using residues linked to N-hydroxysuccinimide (by the method well-known to a person skilled in the art and described in US 2006004185). Finally, the protective groups are removed. The acylated polymyxin D nonapeptide carries only three (3) free amino groups, all in the heptapeptide ring portion.

In an analogous manner, acylated polymyxin S nonapeptide can be made. It carries only three (3) free amino groups.

3. Totally synthetic polymyxin and octapeptin derivatives can be made by the very conventional methods known for those skilled in the art. Such methods include the liquid-phase synthesis procedures as well as the solid-phase synthesis procedures described for instance by Sakura et al. (2004), Tsubery et al. (2000a, 2000b, 2002, 2005), and Ofek et al. (2004). The methods include e.g. the use of protecting agents such as Fmoc, tBoc, and CBZ at strategic positions, as well as the cyclisation step where DPPA (diphenyl phosphorazidate) or a mixture of benzotrizole-1-yl-oxy-tris-pyrrolidinophosphonium hexafluorophosphate (PyBop), N-hydroxybenzotriazole (HoBt), and N-methylmorpholine (NMM) is used. Fmoc derivatives of many non-trivial as well as D-amino acids are commercially available. The amino terminus of the last amino acid residue is left unprotected to enable direct reaction in the acylation procedure with acids such as propionic acid, butyric acid, isobutyric acid, valeric acid, and isovaleric acid.

4. Acylation of the free N-terminal alpha-amino group of the intermediate compounds described above (paragraphs 1-3) can also be performed by using anhydrides such as acetic anhydride (see Example 1), propionic anhydride, butyric anhydride, and valeric anhydride by using conditions well-known to a person skilled in the art. N-formylation can be performed by using p-nitrophenyl formate in N-methylpyrrolidine and conditions well-known to a person skilled in the art. N-methylation can be performed by using a mixture of formic acid and acetic anhydride in dimethylformamide and conditions well-known to a person skilled in the art.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

LIST OF REFERENCES

All references cited in the present application are hereby incorporated by reference in their entirety.

Chihara S, Tobita T, Yahata M, Ito A, Koyama Y. 1973. Enzymatic degradation of colistin. Isolation and identification of α-N-Acyl α,γ-diaminobutyric acid and colistin nonapeptide. Agr Biol Chem 37:2455-2463.

Chihara S, Ito A, Yahata M, Tobita T, Koyama Y. 1974. Chemical synthesis, isolation and characterization of α-N-fattyacyl colistin nonapeptide with special reference to the correlation between antimicrobial activity and carbon number of fattyacyl moiety. Agric Biol Chem 38:521-529.

de Visser P C, Kriek N M A J, van Hooft P A V, Van Schepdael A, Filippov D V, van der Marel G A, Overkleeft H S, van Boom J H, Noort D. 2003. Solid-phase synthesis of polymyxin $B_1$ and analogues via a safety-catch approach. J. Peptide Res. 61:298-306.

Kimura Y, Matsunaga H, Vaara M. 1992. Polymyxin B octapeptide and polymyxin B heptapeptide are potent outer membrane permeability-increasing agents. J Antibiot 45:742-749.

Kurihara T, Takeda H, Ito H, Sato H, Shimizu M, Kurosawa A. 1974. Studies on the compounds related to colistin. IX. On the chemical deacylation of colistin and colistin derivatives. Yakugaku Zasshi 94:1491-1494.

Li J, Milne R W, Nation R L, Turnidge J B, Smeaton T C, and Coulthard K. 2003. Use of high-performance liquid chromatography to study the pharmacokinetics of colistin sulfate in rats following intravenous administration. Antimicrob Agents Chemother 47:1766-1770.

Li J, Milne R W, Nation R L, Turnidge J B, Smeaton T C, and Coulthard K. 2004. Pharmacokinetics of colistin methanesulphonate and colistin in rats following an intravenous dose of colistin methanesulphonate. J Antimicrob Chemother 53:837-840.

Nagai J, Saito M, Adachi Y, Yumoto R, Takano M. 2006. Inhibition of gentamicin binding to rat renal brush-border membrane by megalin ligands and basic peptides. J Control Release 112:43-50.

Nikaido H. 2003. Molecular basis of bacterial outer membrane permeability revisited. Microbiol. Molec Biol Rev 67:593-656.

Nikaido H, Vaara M. 1985. Molecular basis of bacterial outer membrane permeability. Microbiol. Rev 49:1-32.

Okimura K, Ohki K, Sato Y, Ohnishi K, Uchida Y, Sakura N. 2007. Chemical conversion of natural polymyxin B and colistin to their N-terminal derivatives. Bull. Chem. Soc. Jpn. 80 (No. 3):543-552.

Rose F, Heuer K U, Sibelius U, Hombach-Klonisch S, Ladislau K, Seeger W, Grimminger F. 1999. Targeting lipopolysaccharides by the nontoxic polymyxin B nonapeptide sensitizes resistant E. coli to the bactericidal effect of human neutrophils. J Infect Dis 182:191-199.

Sakura N, Itoh T, Uchida Y, Ohki K, Okimura K, Chiba K, Sato Y, Sawanishi H. 2004. The contribution of the N-terminal structure of polymyxin B peptides to antimicrobial and lipopolysaccharide binding activity. Bull Chem Soc Jpn 77:1915-1924.

Srinivasa B D, Ramachandran L K. 1978. Chemical modification of peptide antibiotics: Part VI—Biological activity of derivatives of polymyxin B. Ind J Biochem Biophys 14:54-58.

Srinivasa B D, Ramachandran L K. 1979. The polymyxins. J Scient Industr Res 38:695-709.

Srinivasa B D, Ramachandran L K. 1980. Essential amino groups of polymyxin B. Ind J Biochem Biophys 17:112-118.

Storm D R, Rosenthal K S, Swanson P E. 1977. Polymyxin and related peptide antibiotics. Annu Rev Biochem 46:723-63.

Teuber M. 1970. Preparation of biologically active mono-N-acetyl(14C)-derivatives of the membrane-specific polypeptide antibiotic polymyxin B. Z Naturforsch 25b:117.

Tsubery H, Ofek I, Cohen S, Fridkin M. 2000a. Structure-function studies of polymyxin B nonapeptide: Implications to sensitization of Gram-negative bacteria. J. Med Chem 43:3085-3092.

Tsubery H, Ofek I, Cohen S, Fridkin M. 2000b. The functional association of polymyxin B with bacterial lipopolysaccharide is stereospecific: Studies on polymyxin B nonapeptide. Biochemistry 39:11837-11844.

Tsubery H, Ofek I, Cohen S, Fridkin M. 2001. N-terminal modifications of polymyxin B nonapeptide and their effect on antibacterial activity. Peptides 22:1675-1681.

Tsubery H, Ofek I, Cohen S, Eisenstein M, Fridkin M. 2002. Modulation of the hydro-phobic domain of polymyxin B nonapeptide: effect on outer-membrane permeabilization and lipopolysaccharide neutralization. Molecular Pharmacology 62:1036-42.

Tsubery H, Yaakov H, Cohen S, Giterman T, Matityahou A, Fridkin M, Ofek I. 2005. Neopeptide antibiotics that function as opsonins and membrane-permeabilizing agents for gram-negative bacteria. Antimicrob Agents Chemother 49:3122-3128.

Vaara M. 1992. Agents that increase the permeability of the outer membrane. Microbiol. Rev 56:395-411.

Vaara M. 1993. Antibiotic-supersusceptible mutants of *Escherichia coli* and *Salmonella typhimurium*. Antimicrob Agents Chemother 37:2255-2260.

Vaara M, Vaara T. 1983a. Sensitization of Gram-negative bacteria to antibiotics and complement by a nontoxic oligopeptide. Nature (London) 303:526-528.

Vaara M, Vaara T. 1983b. Polycations sensitize enteric bacteria to antibiotics. Antimicrob Agents Chemother 24:107-113.

Vaara M, Vaara T. 1983c. Polycations as outer membrane-disorganizing agents. Antimicrob Agents Chemother 24:114-122.

Vaara M, Viljanen P, Vaara T, Makela P. 1984. An outer membrane disorganizing peptide PMBN sensitizes E. coli strains to serum bactericidal action. J Immunol 132:2582-2589.

Viljanen P, Matsunaga H, Kimura Y, Vaara M. 1991. The outer membrane permeability-increasing action of deacylpolymyxins. J Antibiotics 44:517-523.

EXAMPLES

The following examples illustrate certain embodiments of the present invention and should not be construed as limiting the scope of the invention.

Example 1

Peptide Synthesis

Polymyxin derivatives ("NAB peptides" or "NAB compounds") were synthesized by conventional solid phase chemistry, using the standard Fmoc protection strategy. The amino acid at the C-terminus is commercially available as pre-attached to the solid phase and when cleaved off the resin with acid, yields a C-terminal carboxylic acid.

The strategy in the protection was to use three levels of orthogonal protection, temporary Fmoc protection for the alpha amino functions, groups which are removed during the acid cleavage stage, and semi-permanent protection to cover reactive side chain functions while the cyclisation reaction takes place. After cleavage of the peptide from the resin, the C-terminal carboxylic acid is reacted with an amino function on the side chain of one of the amino acids to form a cyclic peptide. After the cyclisation step, the semi-permanent protection groups are removed to yield NAB peptide.

Accordingly, the alpha amino function of the amino acid was protected by fluorenyl-methoxycarbonyl (Fmoc) and Fmoc was removed by 20% piperidine in dimethylformamide (DMF) at every cycle. The amino acid that is involved with cyclisation, i.e., diaminobutyric acid, was protected by t-butoxycarbonyl (tBoc), an acid labile group which was removed at the cleavage step. The functional group of asparagine was protected by tritylation. All the other amino acids which have functional side chain groups were protected by a group that is stable to the acid cleavage stage, i.e., benzyloxycarbonyl (Z). Amino acids phenylalanine and leucine naturally needed no side chain protection. The amino terminus was not protected; this enabled direct reaction in the acylation procedure.

The synthesis steps were performed in a commercial automatized synthesizer that employed O-(6-Chlorobenzotriazol-1-yl)-N,N,N',N'-tetramethyluronium hexafluorophosphate (HCTU) as activator.

The acylation was performed by using a four-fold molar excess of each amino acid or the fatty acid, four-fold molar excess of the activator HCTU (see above), and an eight-fold molar excess of N-methyl morpholine. The reaction time was 30 min.

The amino acids were purchased already protected from standard suppliers.

The peptide was removed from the resin by reaction with a solution of 95% trifluoroacetic acid and 5% water for 2 hours at room temperature, to yield the partially protected product. The resulting peptide was precipitated with diethyl ether.

The cyclisation mixture used was benzotriazole-1-yl-oxy-tris-pyrrolidino-phosphonium hexafluorophosphate (Py-Bop), N-hydroxybenzotriazole (HoBt), and N-methyl morpholine (NMM) at the molar excess of 2, 2, and 4, respectively. The peptide was dissolved in dimethylformamide, the cyclisation mix was added and allowed to react for 2 hours. The cyclised, protected peptide was precipitated by the addition of cold diethyl ether. Any residual PyBop was removed by washing the peptide with water.

Acetylation for performed by using acetic anhydride-diisopropylethylamine-DMF (1:1:18 by vol.).

The remaining side chain protection groups (Z) were removed by catalytic dehydrogenation. The peptide was dissolved in acetic acid-methanol-water (5:4:1), under an atmosphere of hydrogen and in the presence of a palladium charcoal catalyst.

The peptide was purified by reverse phase chromatography using conventional gradients of acetonitrile:water:trifluoroacetic acid. The product was dried by lyophilisation.

The yield was 10-20 mg representing approx. 10%-20% of the theoretical, calculated from the molar amount (approx. 100 micromoles) of the first amino acyl residue bound to the resin.

The purity, as estimated by reversed phase HPLC was more than 90%. Within experimental error, the masses obtained were those expected from the theoretical values.

Example 2

Activity of the Compounds Against *Escherichia coli* and *Pseudomonas aeruginosa*

Peptides synthesized in Example 1, both carrying only three (3) positive charges, were studied for their ability to sensitize *E. coli* to the model antibiotic rifampin. This was tested employing LB agar (LB Agar Lennox, Difco, BD, Sparks, Md., U.S.A) plates that contain increasing concentrations (0.1 µg/ml, 0.3 µg/ml, 1 µg/ml) of rifampin (Sigma-Aldrich, St. Louis, Mo., U.S.A) as well as by using LB agar control plates that did not contain rifampin. The indicator organism *E. coli* IH3080 (K1:O18) was an encapsulated strain originally isolated from a neonate suffering from meningitis (Vaara et al. 1984) and obtained from National Public Health Institute, Helsinki, Finland.

From an overnight-grown culture of IH3080 on LB agar, a suspension of approx. $10^8$ cells/ml was prepared in 0.9% NaCl. Aliquots of this suspension were then pipetted on the agar plates and the plates were gently shaken to spread the suspension evenly on the entire surface of the plate. Thereafter, the unabsorbed part of the suspension was removed by using a Pasteur pipette. After the surface had dried, small wells (diameter, 2 mm) were drilled on the plates (five wells per plate) by using a sterile sharp-edged narrow metal tube, single-use pipette tip, and vacuum suction. Alternatively, a swab was used to spread the inoculum. Samples (4 µl and 10 µl) of the peptide solution in 0.9% NaCl (at concentrations of 1 µg/ml and 0.1 µg/ml) were then pipetted to the wells and the sample fluids were allowed to absorb. Controls included 0.9% NaCl solution without the compound to be tested. The plates were then incubated for 18 h at 37° C. whereafter the diameters of growth inhibition zones around each well were measured; the diameter of the well itself was not reduced. Finally, the diameters were converted to surface areas of growth inhibition (in square mm).

Table 2 shows the activity of the novel compounds against *E. coli* IH3080 as compared with that of control compounds. Even though both lacked the direct antibacterial activity of NAB739, they sensitized at a concentration of 4 µg/ml the target to a concentration of rifampin as low as 0.1 µg/ml. Interestingly, NAB747 was directly antibacterial against *P. aeruginosa* ATCC 27853. In a well containing 10 µg of the peptide, it caused a zone of inhibition with the surface area of 50 sq mm. At 4 µg, the corresponding value was 20 sq mm.

TABLE 2

Structure of the novel compounds and their activity agains *E. coli* IH3080

| Compound group | Compound name | SEQ ID NO. | Structure* FA-part | Peptide sequence side chain | cyclic part | Positive charges total (cyclic) | Direct activ- ity** | Activity w. rifampin*** |
|---|---|---|---|---|---|---|---|---|
| Control compounds | Polymyxin B | 1 | MO(H)A | XTX | cy[XXfLXXT] | 5 (3) | 79 | 95 |
| | Deacyl- | 2 | | | cy[XXfLXX | | | |

TABLE 2-continued

Structure of the novel compounds and their activity agains E. coli IH3080

| Compound group | Compound name | SEQ ID NO. | Structure* FA-part | side chain | cyclic part | Peptide sequence cyclic part | Positive charges total (cyclic) | Direct activ-ity** | Activity w. rifampin*** |
|---|---|---|---|---|---|---|---|---|---|
| | polymyxin B | | — | +XTX | | cy[XX1LXXT] | 6 (3) | 57 | 79 |
| | Deacylcolistin | 3 | — | +XTX | | cy[XX1LXXT] | 6 (3) | 79 | 87 |
| | Polymyxin B nonpeptide | 4 | — | +TX | | cy[XXfLXXT] | 5 (3) | 0 | 20 |
| | Polymyxin B heptapeptide | 5 | — | + | | cy[XXfLXXT] | 4 (4) | 0 | 0 |
| | NAB 704 | 6 | — | +TZ | | cy[XXfLXXT] | 4 (3) | 0 | 0 |
| | NAB 705 | 7 | — | +ZTZ | | cy[XXfLXXT] | 4 (3) | 0 | 0 |
| | NAB 701 | 8 | — | +TX | | cy[XXfLZZT] | 3 (1) | 0 | 0 |
| | NAB 702 | 9 | — | +TX | | cy[XXfLBBT] | 3 (1) | 0 | 0 |
| | NAB 703 | 11 | — | +TX | | cy[XXfLJJT] | 3 (1) | 0 | 0 |
| | Octanoyl PMBH | 12 | OA | — | | cy[XXfLXXT] | 3 (3) | 0 | 0 |
| | NAB 736 | 13 | DA | — | | [XXfLXXT] | 3 (3) | 0 | 113 |
| | NAB 739 | 14 | OA | Ts | | cy[XXfLXXT] | 3 (3) | 133 | 177 |
| | NAB 740 | 15 | DA | Ts | | cy[XXfLXXT] | 3 (3) | 95 | 95 |
| | NAB 7061 | 16 | OA | TZ | | cy[XXfLXXT] | 3 (3) | 0 | 113 |
| Novel compounds | NAB 741 | 29 | Ac | Ts | | cy[XXfLXXT] | 3 (3) | 0 | 95 |
| | NAB 745 | 28 | Ac | Tn | | cy[XXfLXXT] | 3 (3) | 0 | 50 |
| | NAB 747 | 10 | Me | Ts | | cy[XXfLXXT] | 4 (3) | 0 | 28 |

*One-letter codes for amino acyl residues: F, Phe; L, Leu; N, Asn; S, Ser; T, Thr; X Dab; Z, Abu; B, N-gammaformyl-Dab; J, N-gamma-acetyl-Dab. Small letters indicate residues that are in D-configuration.
+ indicates the positive charge of the alpha-amino group in the free N-terminus of the peptide.
Abbreviations: MO(H)A, the mixture of 6-methyloctanoyl, 6-methylheptanoyl and related fatty acid residues occurring in polymyxin B; OA, octanoyl; DA, decanoyl; Ac, acetyl; Me, methy.
**Antibacterial activity measured as the growth inhibition (in square millimeters) around a well containing 4 micrograms of the compound on LB plates.
***Antibacterial activity measured as the growh inhibition (in square millimeters) around a well containing 4 micrograms of the compound on a LB plate containing rifmpin (0.1 micrograms/ml).

Example 3

NAB741 Sensitizes *E. Coli, Klebsiella Pneumoniae*, and *Enterobacter Cloacae* to a Broad Range of Antibacterial Agents The minimum inhibitory concentrations (MIC) of a representative set of clinically used antimicrobial agents were determined for two strains of *E. coli* (ATCC25922 and IH3080), *K. pneumoniae* ATCC13883, and *E. cloacae* ATCC23355 by using Mueller-Hinton agar medium (product no Lab039; LabM Ltd., Bury, Lancs, U.K.) in the presence of NAB741 (4 µg/ml) as well as in its absence. MICs were determined by using E-strips (Biodisk Ltd., Solna, Sweden) according to the manufacturer's instructions. The NAB741 concentration used did not itself inhibit the growth of the target bacteria. The MIC of NAB741 for all these strains was >16 µg/ml.

The results are shown in Table 3. NAB741 at a concentration of 4 µg/ml was able to sensitize the tested strains to rifampin by a factor ranging from >64 to >2000. Sensitization factor is defined as the ratio of the MIC of an antibiotic in the absence of NAB741 to that in the presence of 4 µg/ml of NAB741. Extremely high sensitization factors were observed also to clarithromycin (24-340), mupirocin (8-192), azithromycin (16-32), for some of the strains to fusidic acid (128-170), and for *E. cloacae* to vancomycin (170). All these antibacterial agents are notably hydrophobic or large (vancomycin) and are known to be excluded by the intact OM of Gram-negative bacteria but penetrate the damaged OM.

TABLE 3

Sensitization factors* to selected antibacterial agents at NAB 741 concentration of 4 µg/ml

| | E. coli ATCC 25922 | E. coli IH 3080 | K. pneum. ATCC 13883 | E. cloacae ATCC 23355 |
|---|---|---|---|---|
| Rifampin | 750 | 250 | >64 | >2000 |
| Clarithromycin | 340 | 96 | 24 | 96 |
| Mupirocin | 128 | 64 | 8 | 190 |
| Azithromycin | 24 | 32 | 32 | 16 |
| Fusidic acid | 170 | 130 | >5 | >130 |
| Vancomycin | >16 | 16 | >2 | 170 |

*Sensitization factor is the ratio of the MIC of the antibiotic in the absence of NAB 741 to that in the presence of 4 µg/ml of NAB 741

Example 4

Susceptibility of Seven Different Strains of Gram-Negative Bacteria to Rifampin and Clarithromycin in the Presence of NAB741 (4 µg/ml)

The minimum inhibitory concentrations (MIC) of rifampin and clarithromycin for a representative set of different strains of clinically relevant Gram-negative bacteria were determined by the E-test method as in Example 3 and by using Mueller-Hinton agar with or without NAB741 (4 µg/ml). This concentration of NAB741 did not itself inhibit the growth of the target bacteria. Five of the strains originated from ATCC. *Acinetobacter baumannii* F264 was purchased from Mobidiag Ltd., Helsinki, Finland. The source of *E. coli* IH3080 has been given in Example 2.

The results are shown in Table 4. It shows that NAB 741 is remarkably active even against *Acinetobacter baumannii*.

TABLE 4

The ability of NAB 741 to sensitize Gram-negative bacteria to model antibiotics (rifampin and clarithromycin)

| Bacterial strain | MIC (µg/ml) of rifampin in the presence of 4 µg/ml of NAB 741* | Sensitization factor* to rifampin | MIC (µg/ml) of clarithromycin in the presence of 4 µg/ml of NAB 741 | Sensitization factor** to clarithromycin |
|---|---|---|---|---|
| E. coli ATCC25922 | 0.016 | 750 | 0.125 | 340 |
| E. coli IH3080 | 0.047 | 250 | 0.125 | 96 |
| K. pneumoniae ATCC13883 | 0.5 | >64 | 1 | 24 |
| E. cloacae ATCC23355 | 0.016 | 2000 | 0.5 | 96 |
| Ac. baumannii ATCC19606 | 0.19 | 16 | 0.5 | 32 |
| Ac. baumannii F264 | 0.125 | 64 | 0.5 | 32 |
| P. aeruginosa ATCC27853 | 16 | 2 | 64 | 2 |

*The ratio of rifampin MIC in the absence of NAB 741 to that in the presence of NAB 741 (4 µg/ml).
**The ratio of clarithromycin MIC in the absence of NAB 741 to that in the presence of NAB 741 (4 µg/ml).

Example 5

NAB741 Sensitizes a Meropenem-Resistant Strain of *Acinetobacter baumannii* to Meropenem The minimum inhibitory concentrations (MIC) of meropenem for two strains of *A. baumannii* were determined by the E-test method as in Example 4 and by using Mueller-Hinton agar with or without NAB741 (4 µg/ml). This concentration of NAB741 did not itself inhibit the growth of the target bacteria. Sensitization factor was defined as in Example 4. The results are shown in Table 5. NAB7061 sensitized the meropenem-resistant strain F264 to meropemen by a factor >4.

TABLE 5

Sensitization of the meropenem-resistant strain of *Acinetobacter baumannii* to meropenem in the presence of NAB 741 (4 µg/ml)

| | MIC (µg/ml) of meropenem at the indicated concn (µg/ml) of NAB 741 | |
|---|---|---|
| Strain | 0 | 4 |
| A. baumannii ATCC19606 | 0.75 | 0.5 |
| A. baumannii F264 | >32 | 8 |

Example 6

NAB741 Sensitizes *E. coli* to the Complement in Fresh Normal Serum

The ability of NAB741 to sensitize encapsulated, smooth strain of *E. coli* to the bactericidal action of normal guinea pig serum (GPS) was studied by the method described by Vaara et al. (1984). *E. coli* IH3080 (O18,K1) was grown in LB broth (LB broth Lennox, Difco, BD, Sparks, Md., U.S.A) at 37° C. in a rotary shaker into early logarithmic growth phase, washed with PBS (phosphate-buffered saline, 8.0 g of NaCl, 0.2 g of KCl, 1.44 g of $Na_2HPO_4 \times 2H_2O$ and 0.2 g of $KH_2PO_4$ per liter) and resuspended in PBS, to approx. $10^9$ cells/ml). GPS was used as complement source. It was stored at −70° C. before use. To inactive the complement, serum was incubated at 56° C. for 30 min.

The experimental procedure was as follows. 10% GPS in PBS was inoculated with approx. 500 CFU (colony forming units) of bacteria per ml and pipetted in 0.2 ml aliquots into wells of microtiter plates. The wells already contained increasing amounts of NAB7061 in 0.020 ml of 0.9% NaCl. The plate was incubated at 37° C. for 2 h whereafter each well was emptied onto LB plates. The plates were incubated overnight at 37° C. and the developed colovies were counted.

The results are shown in Table 6. NAB741 itself did not significantly reduce CFU count in the absence of GPS or in the presence of heat-inactivated 10% GPS. However, as low a concentration of NAB741 as 2 µg/ml was sufficient to reduce CFU count by a factor of approx. 100 in the presence 10% fresh GPS. Accordingly, NAB741 acts synergistically with the bactericidal complement machinery present in fresh serum, as does PMBN, the agent well known to have this property.

TABLE 6

The synergistic bactericidal activity of NAB741 and 10% guinea pig serum (GPS) against *E. coli* IH3080 (O18:K1)*

| | Concentration of NAB741 (µg/ml) | | | |
|---|---|---|---|---|
| | 0 | 1 | 2 | 4 |
| none (PBS) | 100 | 71 | 86 | 58 |
| 10% GPS | >200 | 5 | 7 | 0 |
| 10% GPS, heat inactivated | >200 | >200 | >200 | 125 |

*measured as % survival after 2-hour treatment at 37° C.

Example 7

Preparation and Biological Activity of NAB 739 Methanesulfonate Sodium Salt

NAB 739 acetate (100 mg) was dissolved in water (2 ml) and neutral formaldehyde solution (400 microliters of 30% aqueous formaldehyde [brought to pH 7.2 with 1 N Na—HCO3]) was added. Then, 1 N NaHCO3 solution (2 ml) was added, and the precipitated NAB 739 formaldehyde derivative was filtered and washed with water. The moist solid was suspended in water (5 ml), and sodium metabisulphite (100 mg) was added. A clear solution was obtained after a few minutes and was freeze-dried. The flocculent white solid was extracted with warm acetone (7.5 ml) and dried in vacuo. The yield was 56 mg. Analysis of the product by ESI mass spectrometry revealed a predominant peak with the molecular mass of 1075.3 indicating that most of the derivative was sulfomethylated at each of the three Dab residues of the NAB 739 compound. A minor peak representing the NAB 739 blocked randomly at two of the three Dab residues was also visible.

For the measurement of the antibacterial activity of aqueous solutions of NAB 739 methanesulfonate sodium, three different solutions were made: 1) A solution (1 mg/ml) made in 0.9% NaCl immediately prior to the experiment, 2) a solution (1 mg/ml) made in 0.9% NaCl 24 h prior to the experiment and kept at 37° C., 3) a solution (1 mg/ml) made in 0.9% NaCl 48 h prior to the experiment and kept at 37° C. A freshly made solution of NAB 739 acetate served as the control compound.

TABLE 7

The bactericidal activity of NAB 739 methanesulfonate as compared with that of NAB 739 against *E. coli* IH3080*

| Compound | Solution age | 0 | 1 | 2 | 4 |
|---|---|---|---|---|---|
| NAB 739 MS** | fresh | 100 | 70 | 62 | 16 |
| NAB 739 MS** | 24 h | | 55 | 34 | 6 |
| NAB 739 MS** | 48 h | | 35 | 11 | 0 |
| NAB 739 | fresh | | 21 | 2 | 0 |

*measured as % survival after 2-hour treatment at 37 degrees centigrade.
**MS, methanesulfonate The test bacterium was *E. coli* IH3080. It was grown in LB broth (LB broth Lennox, Difco, BD, Sparks, Md., U.S.A.) at 37° C. in a rotary shaker into early logarithmic growth phase, washed with PBS, and resuspended in PBS to approx. 10e9 cells/ml. PBS was inoculated with approx. 500 CFU (colony forming units) of bacteria per ml and pipetted in 0.2 ml aliquots into wells of a microtiter plate. The plates already contained increasing concentrations of NAB 739 methanesulfonate or the control compound in 0.020 ml of 0.9% NaCl. The plate was incubated at 37° C. for 1 h whereafter each well was emptied onto LB plates. The plate was incubated overnight at 37° C. and the developed colonies were counted.

The results are shown in Table 7. The fresh solution of NAB 739 methanesulfonate was much less antibacterial than the control compound NAB 739. Keeping the NAB 739 methanesulfonate solution at 37° C. for 24 h prior to use slightly increased the activity whereas keeping for 48 h resulted in activity almost equal to that observed with the control compound. These results indicate that NAB 739 methanesulfonate, in analogy with colistin methanesulfonate, slowly decomposes in aqueous solutions to yield antibacterially more active substances, i.e., less sulfomethylated substances and eventually free NAB 739.

Similarly, methanesulfonate derivatives of NAB 741, NAB 745, NAB 747 and other compounds described as herein are prepared. These prodrugs decompose in vivo to yield compounds which possess the ability to sensitize target bacteria to other antibacterial agents and serum complements.

Example 8

Comparison of Basic Pharmakokinetic Properties of NAB 741 and NAB 739

The studies were principally performed by using the methods described by Li et al. (2003, 2004). Each rat (n=4 for both compounds, Sprague-Dawley, male) was anaesthetized using isoflurane, and a polyethylene cannula was inserted into the jugular vein. Each rat was placed into a metabolic cage and allowed to recover from the procedure overnight. The test compound (acetate, 1 mg/kg) was administered as a bolus (in 200 µl sterile 0.9% saline) through the cannula, followed by washing with 0.8 nil of saline. Nine blood samples (0, 10, 20, 30, 60, 90, 120, 180, and 240 min), each 200 µl, were manually collected through the cannula. When collecting samples, the first 100 µl of blood was withdrawn and kept in the syringe. After collecting the actual sample with another syringe, the content of the first syringe was returned to the rat together with 400 µl of heparinized saline. Blood samples were centrifuged to obtain plasma. Urine samples were collected in 0-4 h, 4-6 h, and 6-24 h intervals. Plasma and urine samples were stored at −80° C.

The samples were analyzed using liquid chromatography and mass spectrometry with electrospray ionization interface (LC/electrospray ionization MS). To a 100-µl sample, 10 µl of internal standard (NAB 739, 80 µg/ml) and 200 µl (plasma samples) or 100 µl (urine samples) of acetonitrile was added, the mixture was vortex-mixed for 1 min, and centrifuged at 10.000 g for 10 min. The chromatography employed the HPLC C18 column (50×2 mm), 0.1% formic acid as the solvent A, 0.1% acetonitrile as the solvent B, flow rate of 0.2 ml/min, and the following gradient: 5%-30% B in 6 min, 30%-90% B in 0.5 min, 90% B held for 2.5 min, 90%-5% B in 1 min. The eluent between 5.90-7.00 min and 9.00-10.1 min was directed to the MS system using a switching valve. The positive protonated molecular ions of NAB 741 at m/z 496.7 and 331.4 and of NAB 739 at m/z=538.8 and 359.6 and were monitored. NAB 741 was eluted at 6.65±0.05 min and NAB739 was eluted at 9.45±0.05 min. Non-compartmental analysis of the compounds in plasma was performed using WinNonlin software (version 4.0, Mountain View, Calif., USA), with the model of NA201 (i.v. bolus input for plasma data).

The basic pharmacokinetic parameters determined for NAB 741, were as follows: half-life (min), 32.7±2.41; volume of distribution (ml/kg), 243 ±24.0; clearance (ml/min/kg), 7.39±0.85; urinary recovery (% of dose in 24 h), 50.9±13.6; and renal clearance (ml/min/kg), 3.78±1.11.

The basic pharmacokinetic parameters determined for NAB 739, a compound otherwise identical to NAB 741 but having octanoyl residue instead of acetyl residue as its terminal moiety, were as follows: half-life (min), 69.0±21.9; volume of distribution (ml/kg), 222±20.5; clearance (ml/min/kg), 2.63±0.54; urinary recovery (% of dose in 24 h), 19.4±7.38; and renal clearance (ml/min/kg), 0.53±0.30.

The corresponding parameters for colistin, as determined by $L^1$ et al. (2003) by using an identical dosing and administration procedure, are the following: half-life (min), 74.6±13.2; volume of distribution (ml/kg), 496±60; clearance (ml/min/kg), 5.2±0.4; urinary recovery (% of dose in 24 h), 0.18±0.14; and renal clearance (ml/min/kg), 0.010±0.008.

The invention claimed is:

1. A method for developing novel antibiotics comprising the steps of a) providing a natural polymyxin or octapeptin compound, or a derivative thereof, having a total of 4 to 6 positive charges and a terminal moiety (D) comprising a total of 1 to 5 carbon atoms;

b) replacing from 1 to 3 residues carrying one or more positive charges with a residue not having a positive charge, or with a covalent bond, thereby generating a derivative of a polymyxin compound having 3 positive charges and a terminal moiety (D) comprising a total of 1 to 5 carbon atoms;

c) assaying said polymyxin derivative for the ability to sensitize Gram-negative bacteria to an antibacterial agent; and d) selecting compounds having the ability to sensitize Gram-negative bacteria to an antibacterial agent, wherein the selected compounds are of formula (I):

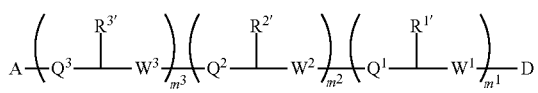
(I)

wherein:

A is a polymyxin ring moiety having the following formula:

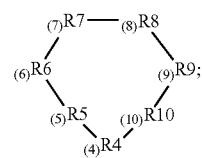

wherein R4 of the polymyxin ring moiety is an amino acid residue selected from the group consisting of lysine, hydroxylysine, ornithine, glutamate, aspartate, an α, γ-diamino-n-butyryl residue, diaminopropionic acid, threonine, cysteine and serine;

R6 is an amino acid residue selected from the group consisting of D-phenylalanine, D-leucine and D-tryptophan;

R7 is an amino acid residue selected from the group consisting of leucine, threonine, phenylalanine, isoleucine, serine, alanine, valine, norvaline, and tryptophan;

R10 is an amino acid residue selected from the group consisting of leucine, threonine, serine, O-acetyl-threonine, O-propionyl-threonine and O-butyryl-threonine; and wherein R5, R8 and R9 are amino acid residues independently selected from the group consisting of an α, γ-diamino-n-butyryl residue, lysine, 2-amino-4-guanido butyric acid, an α-aminobutyryl residue, and threonine;

D is $R^{12}$—(C=O); $R^{12}$—$SO_2$—; $R^{12}$—(C=NH)—; $R^{12}$—NH—(C=S)—; $R^{12}$—NH—(C=O)—; $R_{12}$—NH—(C=NH)—; $R^{12}$—O—(C=S)—; $R^{12}$—O—(C=O); $R^{12}$—P(O) OH—; $R^{12}$—(C=S); or $R^{12\prime}$, wherein $R^{12}$ and $R^{12\prime}$ are alkyl, cycloalkyl, alkenyl, alkynyl, aryl, or aryl alkyl, and wherein D has no more than 1 to 5 carbon atoms;

$m^1$, $m^2$, and $m^3$ are each independently 0 or 1;

$Q^1$, $Q^2$, and $Q^3$ are each independently $CH_2$, C=O, or C=S;

$W^1$, $W^2$, and $W^3$ are each independently $NR^4$, O, or S;

$R^{1\prime}$, $R^{2\prime}$, and $R^{3\prime}$ are each independently side chains of natural or unnatural amino acids, alkyl, alkenyl, alkyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof wherein said derivative has three positive charges at physiological pH; and provided that at least one of $m^1$, $m^2$, and $m^3$ are 1.

2. A method for developing novel antibiotics comprising the steps of:
a) providing a natural polymyxin or octapeptin compound, or a derivative thereof, having a total of 4 to 6 positive charges and a terminal moiety (D) comprising more than 5 carbon atoms;
b) replacing from 1 to 3 residues carrying one or more positive charges with a residue not having a positive charge, or with a covalent bond, thereby generating a derivative of a polymyxin compound having 3 positive charges;
c) replacing said terminal moiety (D) having more than 5 carbon atoms with a terminal moiety (D) comprising a total of 1 to 5 carbon atoms, thereby generating a derivative of a polymyxin compound having 3 positive charges and a terminal moiety (D) comprising a total of 1 to 5 carbon atoms;
d) assaying said polymyxin derivative for the ability to sensitize Gram-negative bacteria to an antibacterial agent; and e) selecting compounds having the ability to sensitize Gram-negative bacteria to an antibacterial agent; and
e) selecting compounds having the ability to sensitize Gram-negative bacteria to an antibacterial agent, wherein the selected compounds are of formula (I):

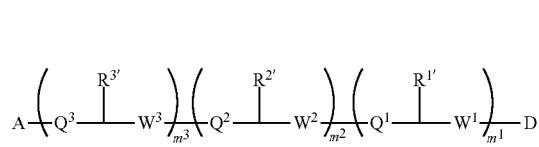

(I)

wherein:
A is a polymyxin ring moiety having the following formula:

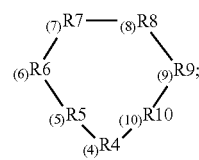

wherein R4 of the polymyxin ring moiety is an amino acid residue selected from the group consisting of lysine, hydroxylysine, ornithine, glutamate, aspartate, an α,γ-diamino-n-butyryl residue, diaminopropionic acid, threonine, cysteine and serine;

R6 is an amino acid residue selected from the group consisting of D-phenylalanine, D-leucine and D-tryptophan;

R7 is an amino acid residue selected from the group consisting of leucine, threonine, phenylalanine, isoleucine, serine, alanine, valine, norvaline, and tryptophan;

R10 is an amino acid residue selected from the group consisting of leucine, threonine, serine, O-acetyl-threonine, O-propionyl-threonine and O-butyryl-threonine; and wherein R5, R8 and R9 are amino acid residues independently selected from the group consisting of an α,γ-diamino-n-butyryl residue, lysine, 2-amino-4-guanido butyric acid, an α-aminobutyryl residue, and threonine;

D is $R^{12}$—(C=O); $R^{12}$—$SO_2$—; $R^{12}$—(C=NH)—; $R^{12}$NH—(C=S)—; $R^{12}$—NH—(C=O)—; $R^{12}$—NH—(C=NH)—; $R^{12}$—O—(C=S)—; $R^{12}$—O—(C=O); $R^{12}$—P(O)OH—; $R^{12}$—(C=S); or $R^{12\prime}$, wherein $R^{12}$ and $R^{12\prime}$ are alkyl, cycloalkyl, alkenyl, alkynyl, aryl, or aryl alkyl, and wherein D has no more than 1 to 5 carbon atoms;

$m^1$, $m^2$, and $m^3$ are each independently 0 or 1;

$Q^1$, $Q^2$, and $Q^3$ are each independently $CH_2$, C=O, or C=S;

$W^1$, $W^2$, and $W^3$ are each independently $NR^4$, O, or S;

$R^{1\prime}$, $R^{2\prime}$, and $R^{3\prime}$ are each independently side chains of natural or unnatural amino acids, alkyl, alkenyl, alkyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof wherein said derivative has three positive charges at physiological pH; and provided that at least one of $m^1$, $m^2$, and $m^3$ are 1.

3. A method for developing novel antibiotics comprising the steps of:
a) providing a natural polymyxin or octapeptin compound, or a derivative thereof, having a total of 4 to 6 positive charges and lacking the terminal moiety (D);
b) replacing from 1 to 3 residues carrying one or more positive charges with a residue not having a positive charge, or with a covalent bond, thereby generating a derivative of a polymyxin compound having 3 positive charges;
c) introducing a terminal moiety (D) comprising a total of 1 to 5 carbon atoms, thereby generating a polymyxin compound having 3 positive charges and a terminal moiety (D) comprising a total of 1 to 5 carbon atoms;
d) assaying said polymyxin derivative for the ability to sensitize Gram-negative bacteria to an antibacterial agent; and
e) selecting compounds having the ability to sensitize Gram-negative bacteria to an antibacterial agent, wherein the selected compounds are of formula (I):

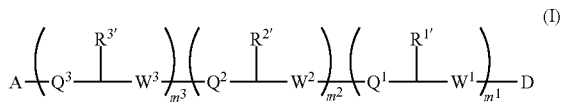

(I)

wherein:
A is a polymyxin ring moiety having the following formula:

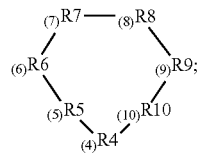

wherein R4 of the polymyxin ring moiety is an amino acid residue selected from the group consisting of lysine, hydroxylysine, ornithine, glutamate, aspartate, an α,γ-diamino-n-butyryl residue, diaminopropionic acid, threonine, cysteine and serine;

R6 is an amino acid residue selected from the group consisting of D-phenylalanine, D-leucine and D-tryptophan;

R7 is an amino acid residue selected from the group consisting of leucine, threonine, phenylalanine, isoleucine, serine, alanine, valine, norvaline, and tryptophan;

R10 is an amino acid residue selected from the group consisting of leucine, threonine serine, O-acetyl-threonine, O-propionyl-threonine and O-butyryl-threonine; and wherein R5, R8 and R9 are amino acid residues independently selected from the group consisting of an α,γ-diamino-n-butyryl residue, lysine, 2-amino-4-guanido butyric acid, an α-aminobutyryl residue, and threonine;

D is $R^{12}$—(C=O); $R^{12}$—$SO_2$—; $R^{12}$—(C=NH)—; $R^{12}$—NH—(C=S)—; $R^{12}$—NH—(C=O)—; $R^{12}$—NH—(C=NH)—; $R^{12}$—O—(C=S)—; $R^{12}$—O—(C=O); $R^{12}$—P(O)OH—$R^{12}$—(C=S); or $R^{12'}$, wherein $R^{12}$ and $R^{12'}$ are alkyl, cycloalkyl, alkenyl, alkynyl, aryl, or aryl alkyl, and wherein D has no more than 1 to 5 carbon atoms;

$m^1$, $m^2$, and $m^3$ are each independently 0 or 1;

$Q^1$, $Q^2$, and $Q^3$ are each independently $CH_2$, C=O, or C=S;

$W^1$, $W^2$, and $W^3$ are each independently $NR^4$, O, or S;

$R^{1'}$, $R^{2'}$, and $R^{3'}$ are each independently side chains of natural or unnatural amino acids, alkyl, alkenyl, alkyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof wherein said derivative has three positive charges at physiological pH; and provided that at least one of $m^1$, $m^2$, and $m^3$ are 1.

4. A method for sensitizing clinically important Gram-negative bacteria to a host defense mechanism complement present in the serum, wherein said bacteria are subjected to the action of a derivative developed according to the method of any one of claims 1, 2 or 3 during a clinical infection.

5. The method according to claim 4, wherein said bacteria are selected from the group consisting of: *Escherichia coli,* *Klebsiella pneumoniae, Klebsiella oxytoca, Enterobacter cloacae, Citrobacter freundii,* and *Acinetobacter baumannii.*

6. A process for preparing a polymyxin derivative of formula (I):

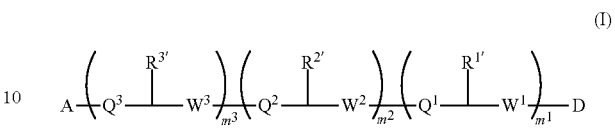

wherein:
A is a polymyxin ring moiety having the following formula:

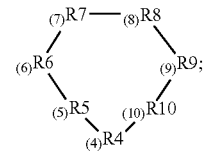

wherein R4 of the polymyxin ring moiety is an amino acid residue selected from the group consisting of lysine, hydroxylysine, ornithine, glutamate, aspartate, an α,γ-diamino-n-butyryl residue, diaminopropionic acid, threonine, cysteine and serine;

R6 is an amino acid residue selected from the group consisting of D-phenylalanine, D-leucine and D-tryptophan;

R7 is an amino acid residue selected from the group consisting of leucine, threonine, phenylalanine, isoleucine, serine, alanine, valine, norvaline, and tryptophan;

R10 is an amino acid residue selected from the group consisting of leucine, threonine, serine, O-acetyl-threonine, O-propionyl-threonine and O-butyryl-threonine; and wherein R5, R8 and R9 are amino acid residues independently selected from the group consisting of an α,γ-diamino-n-butyryl residue, lysine, 2-amino-4-guanido butyric acid, an αaminobutyryl residue, and threonine;

D is $R^{12}$—(C=O); $R^{12}$—$SO_2$—; $R^{12}$—(C=NH)—; $R^{12}$—NH—(C=S)—; $R^{12}$—NH—(C=O)—; $R^{12}$—NH—(C=NH)—; $R^{12}$—O—(C=S)—; $R^{12}$—O—(C=O); $R^{12}$—P(O)OH—; $R^{12}$—(C=S); or $R^{12'}$, wherein $R^{12}$ and $R^{12'}$ are alkyl, cycloalkyl, alkenyl, alkynyl, aryl, or aryl alkyl, and wherein D has no more than 1 to 5 carbon atoms;

$m^1$, $m^2$, and $m^3$ are each independently 0 or 1;

$Q^1$, $Q^2$, and $Q^3$ are each independently $CH_2$, C=O, or C=S;

$W^1$, $W^2$, and $W^3$ are each independently $NR^4$, O, or S;

$R^{1'}$, $R^{2'}$, and $R^{3'}$ are each independently side chains of natural or unnatural amino acids, alkyl, alkenyl, alkyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof wherein said derivative has three positive charges at physiological pH; and provided that at least one of $m^1$, $m^2$, and $m^3$ are 1;

wherein the process comprises:
(A) modifying a natural or synthetic polymyxin or octapeptin compound or a derivative thereof having 4 to 5 positively charged residues and a terminal moiety (D) comprising a total of 1 to 5 carbon atoms by replacing 1 to 2 of said residues by neutral residues, or by a covalent bond, or converting 1 to 2 of said residues into neutral residues in order to obtain a polymyxin derivative of formula (I) having 3 positively charged residues and a terminal moiety (D) comprising a total of 1 to 5 carbon atoms; or
(B) modifying a natural or synthetic polymyxin or octapeptin compound or a derivative thereof having 4 to 5 positively charged residues and a terminal moiety (D) having more than 5 carbon atoms by replacing 1 to 2 of said residues by neutral residues, or by a covalent bond, or converting 1 to 3 of said residues into neutral residues, and by replacing said terminal moiety (D) comprising more than 5 carbon atoms with a terminal moiety (D) comprising a total of 1 to 5 carbon atoms, in order to obtain a polymyxin derivative of formula (I) having a total of 3 positively charged residues and a terminal moiety (D) comprising a total of 1 to 5 carbon atoms, or
(C) modifying a natural or synthetic polymyxin or octapeptin compound or a derivative thereof having 4 to 6 positively charged residues and lacking the terminal moiety (D) by replacing 1 to 3 of said residues by neutral residues, or by a covalent bond, or converting 1 to 3 of said residues into neutral residues, and by introducing a terminal moiety (D) comprising a total of 1 to 5 carbon atoms, in order to obtain a polymyxin derivative of formula (I) having 3 positively charged residues and a terminal moiety (D) comprising a total of 1 to 5 carbon atoms.

7. The process according to claim 6 comprising carrying out the process as a total synthetic process.

8. The process according to claim 6 comprising carrying out the process as a semisynthetic process.

9. The process according to claim 8 comprising the steps of:
   a) subjecting a natural or synthetic polymyxin or octapeptin compound or a derivative thereof to cleavage in order to remove the side chain of said polymyxin compound, and recovering the cyclic part of said compound, and
   b) coupling to the cyclic part obtained in step a) a synthetically prepared side chain in order to obtain the polymyxin derivative of formula (I) according to claim 6.

10. The process according to claim 9 comprising carrying out the cleavage in step a) enzymatically.

11. The process according to claim 9 comprising carrying out the cleavage in step a) chemically.

12. The process according to claim 9 comprising carrying out the cleavage in step a) using a combination of both chemical and enzymatic treatments.

* * * * *

SEQUENCE LISTING

```
<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: Cyclic polypeptide
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: MISC_FEATURE
<222> LOCATION: (1)..(1)
<223> OTHER INFORMATION: Derivatized with a mixture of 6-methyloctanoyl,
      6-methylheptanoyl and related fatty acid residues occurring in
      polymyxin B.
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: VARIANT
<222> LOCATION: (8)..(9)
<223> OTHER INFORMATION: 2,4-Diaminobutyric acid

<400> SEQUENCE: 1

Xaa Thr Xaa Xaa Xaa Phe Leu Xaa Xaa Thr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Circular peptide
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular
<220> FEATURE:
<221> NAME/KEY: MISC_FEATURE
<222> LOCATION: (6)..(6)
<223> OTHER INFORMATION: D-amino acid.
<220> FEATURE:
```

```
<221> NAME/KEY: VARIANT
<222> LOCATION: (8)..(9)
<223> OTHER INFORMATION: 2,4-Diaminobutyric acid

<400> SEQUENCE: 2

Xaa Thr Xaa Xaa Xaa Phe Leu Xaa Xaa Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: 2,4-Diaminobutyric acid

<400> SEQUENCE: 3

Xaa Thr Xaa Xaa Xaa Leu Leu Xaa Xaa Thr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Circular peptide
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (2)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 4

Thr Xaa Xaa Xaa Phe Leu Xaa Xaa Thr
```

```
1               5

<210> SEQ ID NO 5
<211> LENGTH: 7
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (1)..(2)
<223> OTHER INFORMATION: 2,4-Diaminobutyric acid
<220> FEATURE:
<221> NAME/KEY: MISC_FEATURE
<222> LOCATION: (1)..(7)
<223> OTHER INFORMATION: Circular.
<220> FEATURE:
<221> NAME/KEY: MISC_FEATURE
<222> LOCATION: (3)..(3)
<223> OTHER INFORMATION: D-amino acid.
<220> FEATURE:
<221> NAME/KEY: VARIANT
<222> LOCATION: (5)..(6)
<223> OTHER INFORMATION: 2,4-Diaminobutyric acid

<400> SEQUENCE: 5

Xaa Xaa Phe Leu Xaa Xaa Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (2)..(2)
<223> OTHER INFORMATION: Alpha-aminobutyric acid
<220> FEATURE:
<221> NAME/KEY: VARIANT
<222> LOCATION: (3)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 6

Thr Xaa Xaa Xaa Phe Leu Xaa Xaa Thr
1               5

<210> SEQ ID NO 7
<211> LENGTH: 10
<212> TYPE: PRT
<213> ORGANISM: Artificial Sequence
```

-continued

```
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (1)..(1)
<223> OTHER INFORMATION: Alpha-aminobutyric acid
<220> FEATURE:
<221> NAME/KEY: VARIANT
<222> LOCATION: (3)..(3)
<223> OTHER INFORMATION: Alpha-aminobutyric acid
<220> FEATURE:
<221> NAME/KEY: VARIANT
<222> LOCATION: (4)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: 2,4-Diaminobutyric acid

<400> SEQUENCE: 7

Xaa Thr Xaa Xaa Xaa Phe Leu Xaa Xaa Thr
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (2)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: Alpha-aminobutyric acid

<400> SEQUENCE: 8

Thr Xaa Xaa Xaa Phe Leu Xaa Xaa Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Circular peptide.
<220> FEATURE:
```

-continued

```
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (2)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: N-gamma-formyl-diamino-n-butyric acid

<400> SEQUENCE: 9

Thr Xaa Xaa Xaa Phe Leu Xaa Xaa Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with a methyl group.
<220> FEATURE:
<221> NAME/KEY: MISC_FEATURE
<222> LOCATION: (2)..(2)
<223> OTHER INFORMATION: D-amino acid.
<220> FEATURE:
<221> NAME/KEY: VARIANT
<222> LOCATION: (3)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 10

Thr Ser Xaa Xaa Phe Leu Xaa Xaa Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: There is a positive charge on the alpha-amino
      group in the free N-terminus.
<220> FEATURE:
<221> NAME/KEY: VARIANT
<222> LOCATION: (2)..(4)
<223> OTHER INFORMATION: 2,4-Diaminobutyric acid
```

```
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: N-gamma-acetyldiamino-n-butyric acid

<400> SEQUENCE: 11

Thr Xaa Xaa Xaa Phe Leu Xaa Xaa Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with octanoyl.
<220> FEATURE:
<221> NAME/KEY: VARIANT
<222> LOCATION: (1)..(2)
<223> OTHER INFORMATION: 2,4-Diaminobutyric acid
<220> FEATURE:
<221> NAME/KEY: MISC_FEATURE
<222> LOCATION: (1)..(7)
<223> OTHER INFORMATION: Circular.
<220> FEATURE:
<221> NAME/KEY: MISC_FEATURE
<222> LOCATION: (3)..(3)
<223> OTHER INFORMATION: D-amino acid.
<220> FEATURE:
<221> NAME/KEY: VARIANT
<222> LOCATION: (5)..(6)
<223> OTHER INFORMATION: 2,4-Diaminobutyric acid

<400> SEQUENCE: 12

Xaa Xaa Phe Leu Xaa Xaa Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with decanoyl.
<220> FEATURE:
<221> NAME/KEY: VARIANT
<222> LOCATION: (1)..(2)
<223> OTHER INFORMATION: 2,4-Diaminobutyric acid
<220> FEATURE:
<221> NAME/KEY: MISC_FEATURE
<222> LOCATION: (1)..(7)
<223> OTHER INFORMATION: Circular.
<220> FEATURE:
<221> NAME/KEY: MISC_FEATURE
<222> LOCATION: (3)..(3)
<223> OTHER INFORMATION: D-amino acid.
<220> FEATURE:
<221> NAME/KEY: VARIANT
<222> LOCATION: (5)..(6)
<223> OTHER INFORMATION: 2,4-Diaminobutyric acid
```

```
<400> SEQUENCE: 13

Xaa Xaa Phe Leu Xaa Xaa Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with octanoyl.
<220> FEATURE:
<221> NAME/KEY: MISC_FEATURE
<222> LOCATION: (2)..(2)
<223> OTHER INFORMATION: D-amino acid.
<220> FEATURE:
<221> NAME/KEY: VARIANT
<222> LOCATION: (3)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 14

Thr Ser Xaa Xaa Phe Leu Xaa Xaa Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with decanoyl.
<220> FEATURE:
<221> NAME/KEY: MISC_FEATURE
<222> LOCATION: (2)..(2)
<223> OTHER INFORMATION: D-amino acid.
<220> FEATURE:
<221> NAME/KEY: VARIANT
<222> LOCATION: (3)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 15

Thr Ser Xaa Xaa Phe Leu Xaa Xaa Thr
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with octanoyl.
<220> FEATURE:
<221> NAME/KEY: VARIANT
<222> LOCATION: (2)..(2)
<223> OTHER INFORMATION: Alpha-aminobutyric acid
<220> FEATURE:
<221> NAME/KEY: VARIANT
<222> LOCATION: (3)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 16

Thr Xaa Xaa Xaa Phe Leu Xaa Xaa Thr
1               5

<210> SEQ ID NO 17
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: VARIANT
<222> LOCATION: (1)..(1)
<223> OTHER INFORMATION: Gamma-sulphomethylated 2,4-Diaminobutyric acid
<220> FEATURE:
<221> NAME/KEY: MISC_FEATURE
<222> LOCATION: (1)..(1)
<223> OTHER INFORMATION: Derivatized with a mixture of 6-methyloctanoyl,
      6-methylheptanoyl and related fatty acid residues occurring in
      polymyxin B.
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: 2,4-Diaminobutyric acid

<400> SEQUENCE: 17

Xaa Thr Xaa Xaa Xaa Leu Leu Xaa Xaa Thr
1               5                   10

<210> SEQ ID NO 18
<211> LENGTH: 10
```

```
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with a mixture of 6-methyloctanoyl,
      6-methylheptanoyl and related fatty acid residues occurring in
      polymyxin B.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(3)
<223> OTHER INFORMATION: Gamma-sulphomethylated 2,4-Diaminobutyric acid
<220> FEATURE:
<221> NAME/KEY: VARIANT
<222> LOCATION: (4)..(4)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Cicrular.
<220> FEATURE:
<221> NAME/KEY: VARIANT
<222> LOCATION: (5)..(5)
<223> OTHER INFORMATION: Gamma-sulphomethylated 2,4-Diaminobutyric acid
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: Gamma-sulphomethylated 2,4-Diaminobutyric acid

<400> SEQUENCE: 18

Xaa Thr Xaa Xaa Xaa Leu Leu Xaa Xaa Thr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with a mixture of 6-methyloctanoyl,
      6-methylheptanoyl and related fatty acid residues occurring in
      polymyxin B.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (3)..(3)
<223> OTHER INFORMATION: D-amino acid.
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
```

-continued

<222> LOCATION: (8)..(9)
<223> OTHER INFORMATION: 2,4-Diaminobutyric acid

<400> SEQUENCE: 19

Xaa Thr Xaa Xaa Xaa Leu Thr Xaa Xaa Thr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with 6-methyloctanoyl residue.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: 2,4-Diaminobutyric acid

<400> SEQUENCE: 20

Xaa Thr Xaa Xaa Xaa Leu Thr Xaa Xaa Thr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with a mixture of 6-methyloctanoyl,
      6-methylheptanoyl and related fatty acid residues occurring in
      polymyxin B.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: MISC_FEATURE
<222> LOCATION: (3)..(3)
<223> OTHER INFORMATION: D-amino acid.
<220> FEATURE:
<221> NAME/KEY: VARIANT
<222> LOCATION: (4)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Cicrular.
<220> FEATURE:
<221> NAME/KEY: MISC_FEATURE
<222> LOCATION: (6)..(6)
<223> OTHER INFORMATION: D-amino acid.
<220> FEATURE:

```
<221> NAME/KEY: VARIANT
<222> LOCATION: (8)..(9)
<223> OTHER INFORMATION: 2,4-Diaminobutyric acid

<400> SEQUENCE: 21

Xaa Thr Ser Xaa Xaa Leu Thr Xaa Xaa Thr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with 6-methyloctanoyl residue.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: 2,4-Diaminobutyric acid

<400> SEQUENCE: 22

Xaa Thr Xaa Xaa Xaa Leu Ile Xaa Xaa Thr
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with 3-OH-8-methyldecanoic acid.
<220> FEATURE:
<221> NAME/KEY: VARIANT
<222> LOCATION: (1)..(3)
<223> OTHER INFORMATION: 2,4-Diaminobutyric acid
<220> FEATURE:
<221> NAME/KEY: MISC_FEATURE
<222> LOCATION: (2)..(8)
<223> OTHER INFORMATION: Circular.
<220> FEATURE:
<221> NAME/KEY: MISC_FEATURE
<222> LOCATION: (4)..(4)
<223> OTHER INFORMATION: D-amino acid.
<220> FEATURE:
<221> NAME/KEY: VARIANT
<222> LOCATION: (6)..(7)
<223> OTHER INFORMATION: 2,4-Diaminobutyric acid

<400> SEQUENCE: 23

Xaa Xaa Xaa Leu Leu Xaa Xaa Leu
1               5
```

```
<210> SEQ ID NO 24
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: 2,4-Diaminobutyric acid

<400> SEQUENCE: 24

Xaa Thr Xaa Xaa Xaa Leu Leu Xaa Xaa Thr
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: VARIANT
<222> LOCATION: (2)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 25

Thr Xaa Xaa Xaa Leu Leu Xaa Xaa Thr
1               5

<210> SEQ ID NO 26
<211> LENGTH: 10
<212> TYPE: PRT
<213> ORGANISM: Artificial Sequence
<220> FEATURE:
<223> OTHER INFORMATION: Circular peptide.
<220> FEATURE:
<221> NAME/KEY: VARIANT
<222> LOCATION: (1)..(1)
<223> OTHER INFORMATION: 2,4-Diaminobutyric acid
<220> FEATURE:
<221> NAME/KEY: VARIANT
<222> LOCATION: (3)..(5)
<223> OTHER INFORMATION: 2,4-Diaminobutyric acid
<220> FEATURE:
<221> NAME/KEY: MISC_FEATURE
```

```
<222> LOCATION: (4)..(10)
<223> OTHER INFORMATION: Circular.
<220> FEATURE:
<221> NAME/KEY: MISC_FEATURE
<222> LOCATION: (6)..(6)
<223> OTHER INFORMATION: D-amino acid.
<220> FEATURE:
<221> NAME/KEY: VARIANT
<222> LOCATION: (8)..(9)
<223> OTHER INFORMATION: 2,4-Diaminobutyric acid

<400> SEQUENCE: 26

Xaa Thr Xaa Xaa Xaa Phe Leu Xaa Xaa Thr
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Circular peptide.
<220> FEATURE:
<221> NAME/KEY: VARIANT
<222> LOCATION: (1)..(3)
<223> OTHER INFORMATION: 2,4-Diaminobutyric acid
<220> FEATURE:
<221> NAME/KEY: MISC_FEATURE
<222> LOCATION: (2)..(8)
<223> OTHER INFORMATION: Circular.
<220> FEATURE:
<221> NAME/KEY: MISC_FEATURE
<222> LOCATION: (4)..(4)
<223> OTHER INFORMATION: D-amino acid.
<220> FEATURE:
<221> NAME/KEY: VARIANT
<222> LOCATION: (6)..(7)
<223> OTHER INFORMATION: 2,4-Diaminobutyric acid

<400> SEQUENCE: 27

Xaa Xaa Xaa Phe Leu Xaa Xaa Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (1)..(1)
<223> OTHER INFORMATION: Derivatized with an acetyl group.
<220> FEATURE:
<221> NAME/KEY: MISC_FEATURE
<222> LOCATION: (2)..(2)
<223> OTHER INFORMATION: D-amino acid.
<220> FEATURE:
<221> NAME/KEY: VARIANT
<222> LOCATION: (3)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
```

```
<222> LOCATION: (7)..(8)
<223> OTHER INFORMATION: 2,4-Diaminobutyric acid

<400> SEQUENCE: 28

Thr Asn Xaa Xaa Phe Leu Xaa Xaa Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Circular peptide.
<220> FEATURE:
<221> NAME/KEY: MISC_FEATURE
<222> LOCATION: (2)..(2)
<223> OTHER INFORMATION: D-amino acid.
<220> FEATURE:
<221> NAME/KEY: VARIANT
<222> LOCATION: (3)..(4)
<223> OTHER INFORMATION: 2,4-Diaminobutyric acid
<220> FEATURE:
<221> NAME/KEY: MISC_FEATURE
<222> LOCATION: (3)..(9)
<223> OTHER INFORMATION: Circular.
<220> FEATURE:
<221> NAME/KEY: MISC_FEATURE
<222> LOCATION: (5)..(5)
<223> OTHER INFORMATION: D-amino acid.
<220> FEATURE:
<221> NAME/KEY: VARIANT
<222> LOCATION: (7)..(8)
<223> OTHER INFORMATION: 2,4-Diaminobutyric acid

<400> SEQUENCE: 29

Thr Ser Xaa Xaa Phe Leu Xaa Xaa Thr
1               5
```